United States Patent
Korganow et al.

(10) Patent No.: US 10,647,677 B2
(45) Date of Patent: May 12, 2020

(54) ANALOGUES OF HYDROXYCHLOROQUINE (HCQ) WITHOUT RETINAL TOXICITY

(71) Applicants: Inoviem Scientific, Strasbourg (FR); Universite de Strasbourg, Strasbourg (FR); Centre National de la Recherche Scientifique (CNRS), Paris (FR); Centre Internationnal de Recherche aux Frontieres de la Chimie, Strasbourg (FR)

(72) Inventors: Anne-Sophie Korganow, Strasbourg (FR); Pierre Eftekhari, Strasbourg (FR); Alain Wagner, Strasbourg (FR); Corinne Baehr, Illkirch (FR)

(73) Assignees: INOVIEM SCIENTIFIC, Strasbourg (FR); UNIVERSITE DE STRASBOURG, Strasbourg (FR); CENTRE NATIONAL DE LA RECHERCHE SCIENTIFIQUE (CNRS), Paris (FR); CENTRE INTERNATIONAL DE RECHERCHE AUX FRONTIERES DE LA CHIME, Strasbourg (FR)

( * ) Notice: Subject to any disclaimer, the term of this patent is extended or adjusted under 35 U.S.C. 154(b) by 0 days.

(21) Appl. No.: 15/579,324

(22) PCT Filed: Jun. 6, 2016

(86) PCT No.: PCT/EP2016/062816
§ 371 (c)(1),
(2) Date: Dec. 4, 2017

(87) PCT Pub. No.: WO2016/193503
PCT Pub. Date: Dec. 8, 2016

(65) Prior Publication Data
US 2019/0062278 A1    Feb. 28, 2019

(30) Foreign Application Priority Data
Jun. 5, 2015 (FR) ...................... 15 55125

(51) Int. Cl.
C07D 215/46 (2006.01)
A61P 7/00 (2006.01)
A61P 37/06 (2006.01)
A61K 31/4706 (2006.01)
A61K 45/06 (2006.01)
C07D 215/54 (2006.01)

(52) U.S. Cl.
CPC ........ *C07D 215/46* (2013.01); *A61K 31/4706* (2013.01); *A61K 45/06* (2013.01); *A61P 7/00* (2018.01); *A61P 37/06* (2018.01); *C07D 215/54* (2013.01)

(58) Field of Classification Search
None
See application file for complete search history.

(56) References Cited

U.S. PATENT DOCUMENTS 3,362,954 A   1/1968 Surrey

FOREIGN PATENT DOCUMENTS

WO   WO 2005/120437 A2   12/2005

OTHER PUBLICATIONS

Silverman, R. "The Organic Chemistry of Drug Design and Drug Action," 2004, Elsevier, pp. 29-32.*
Toennesmann, E. et al., Immunopharmacol Immunotoxicol. 2013, vol. 35, pp. 434-442.*
Ellames et al., *Synthesis of the Enantiomers of [3-$^3$H]-2-[[4-[(7-Chloro-4-quinoliny)-amino]pentyl]ethylamino]ethanol, [3-$^3$H]-Hydroxychloroquine*, 36(1) Journal of Labelled Compounds and Radiopharmaceuticals 97-102 (1995).
Martirosyan et al., *Differentiation-inducing quinolines as experimental breast cancer agents in the MCF-7 human breast cancer cell model*, 68 Biochemical Pharmacology 1729-1738 (2004).
Surrey et al., *The Synthesis of Some 3-Nitro- and 3-Amino-4-dialkylaminoalkylaminoquinoline Derivatives*, 73(6) Journal of the American Chemical Society 2413-2416 (Jun. 1951).
English translation of the Written Opinion of the International Searching Authority in PCT/EP2016/062816 dated Nov. 29, 2016.

* cited by examiner

*Primary Examiner* — Heidi Reese
(74) *Attorney, Agent, or Firm* — Buchanan Ingersoll & Rooney PC

(57) ABSTRACT

The present invention relates to hydroxychloroquine analogues having an activity superior to that of hydroxychloroquine but free from retinal cytotoxicity of formula (I), their pharmaceutically acceptable salts, solvates or hydrates:

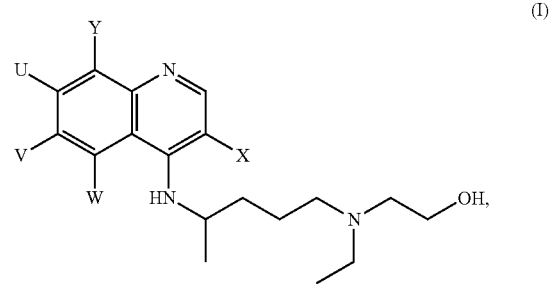

(I)

their method of preparation and their use in the treatment of lupus erythematosus.

28 Claims, 3 Drawing Sheets

Treated mouse with HCQ          Treated mouse with CB137

ANALOGUES OF HYDROXYCHLOROQUINE (HCQ) WITHOUT RETINAL TOXICITY

CROSS-REFERENCE TO RELATED APPLICATIONS

This application is a U.S. National Stage Application pursuant to 35 U.S.C. § 371 of International Patent Application PCT/EP2016/062816, filed on Jun. 6, 2016, and published as WO 2016/193503 on Dec. 8, 2016, which claims priority to French Patent Application 1555125, filed on Jun. 5, 2015, all of which are incorporated herein by reference in their entireties for all purposes.

FIELD OF THE INVENTION

The present invention relates to novel analogues of hydroxychloroquine (HCQ), their use in the treatment of inflammatory and autoimmune diseases, particularly in the treatment of lupus erythematosus, and cancer, as well as the process for the preparation of these compounds.

The invention also relates to a method for screening the activity of compounds useful in the treatment of lupus erythematosus, but not showing retinal toxicity.

STATE OF THE ART

Lupus, also called lupus erythematosus, is a chronic autoimmune disease in which a disorder of the immune system causes tissue damage. This damage includes several forms including subacute lupus erythematosus and systemic lupus erythematosus (SLE). It can affect various organs such as the skin, the joints, the kidneys, the heart, the lungs and sometimes even the brain. The long-term consequences of the disease are serious and can lead to kidney failure (30% of cases) requiring dialysis or even transplantation. The disease progresses by surges, the attacks being interspersed with more or less long periods of remission.

According to the organs affected by the disease, lupus can be expressed very differently from one patient to another. Severe manifestations can be observed in 50% of patients such as inflammation of the kidneys (nephritis), neurological disorders (with psychoses, paralysis, amnesia, depression, headaches, etc.), a lack of red blood cells (anemia) and even platelets (thrombocytopenia). Extremely severe forms of lupus can be life-threatening.

The causes of lupus are still poorly understood, but it is established that the body synthesizes pathogenic autoantibodies that attack certain healthy tissues. Family history shows that the genetic factors are real but various environmental factors contribute to the onset of the pathology (for example, exposure to the sun, tobacco, infection with the Epstein Barr virus in particular). Lupus may also occur after taking medications, especially alpha interferons used for the treatment of certain cancers and chronic viral hepatitis. The latter type of disease is "reversible" because the pathology disappears once the treatment is suspended.

The diagnosis of lupus is difficult because the symptoms are confused with those of other pathologies. Joint damage sometimes leads initially to a diagnostic of rheumatoid arthritis.

Since the fundamental bases of the pathology are not established, the therapeutic solutions currently available are mainly aimed at the best management of the symptoms detected without addressing their causes, preventing lesions to the organs and minimizing the risk of outbreaks during periods of relative stability.

Current therapies are based on the prescription of antimalarial drugs (HCQ) and nonsteroidal anti-inflammatory drugs (NSAIDs) for the mostly cutaneous and articular forms of lupus, the use of corticosteroids, often at high doses, and cytotoxic agents for severe forms (persistent joint symptoms or treatment of visceral forms) and the prescription of immunosuppressants for patients unresponsive to previous treatments. These various treatments, however, have the disadvantage of leading to more or less serious side effects.

Patient management generally combines, over time, different types of medications with most of the time substantive treatment based on the use of HCQ. In recent decades, the only new drug that appeared on the market is Benlysta®, a monoclonal antibody administered as an intravenous infusion which prevents the binding of endogenous BLyS protein, thus inhibiting B cell survival and differentiation.

Benlysta® shows obvious performance limitations and is always used in combination with standard treatment.

Originally designed to treat malaria, 4-aminoquinolines have shown to be effective in the treatment of some of the symptoms of SLE, including fatigue, skin rash and joint pain. The reference molecule is hydroxychloroquine (HCQ, Plaquenil® and generics), generally used at a dose of 400 mg/d. Although the mode of action is still poorly understood, HCQ is the reference treatment for chronic cutaneous lupus.

HCQ, however, has the disadvantage of leading to adverse effects. The most frequent attack is a retinal attack due to the prolonged intake of high doses of this drug. The molecule accumulates in the back (retina) or front (cornea) of the eye, causing accommodation disorders for more than 10% of patients. Retinal deposits can lead to potentially irreversible retinopathies that are able to progress despite discontinuation of treatment. There is currently no treatment for this toxic retinopathy. These potential ocular complications require regular ophthalmic monitoring, at least annually.

There is therefore a need for new small molecules that are more effective than HCQ in the treatment of SLE without retinal toxicity.

Unfortunately, the mode of action of HCQ is not well known to date, in particular the therapeutic and deleterious targets responsible for retinopathy.

The inventors of the present invention have identified a therapeutic target of HCQ, myeloperoxidase (MPO), and a target responsible for retinopathy, which is αB-crystalline (αB-C). The identification of these two targets has allowed the inventors to develop novel HCQ analogues with have a greater inhibitory activity of MPO (therapeutic target) than HCQ and a greater anti-inflammatory activity than HCQ, but having no affinity for αB-crystalline (αB-C). These analogues are characterized, in particular, by the presence of a substituent in position 3 of the quinoline ring of HCQ.

Thus, the compounds of the present invention have lower toxicity than HCQ due to a reduced affinity for αB-crystalline, and therefore do not induce retinal lesions.

FIGURES

COMPOUNDS

Figure 1:
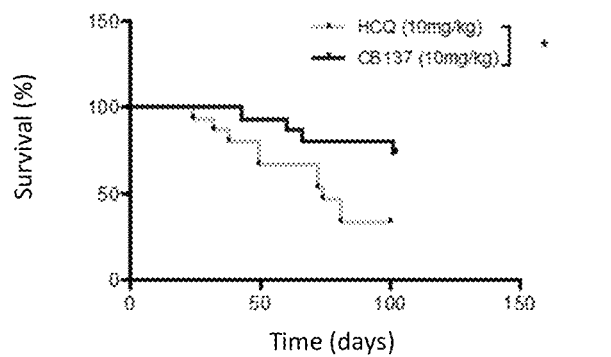
FIG. 1 shows the survival rate of mice treated with HCQ (10 mg/kg) and the compound CB 137 (10 mg/kg).

The present invention therefore relates to novel analogues of the HCQ of formula (I), their pharmaceutically acceptable salts, solvates or hydrates in the form of an enantiomer or a mixture of enantiomers:

(I)

In which U represents:
F, Cl, Br, CN, or $N_3$;
And V, W, X and Y represent independently:
  H provided that V, W, X and Y do not all represent H simultaneously;
  F, Cl, Br, CN or $N_3$;
  $Si(R^a)(R^b)(R^c)$, where
    $R^a$, $R^b$ and $R^c$, which may be identical or different, represent a $C_1$ to $C_6$ alkyl group, preferably $C_1$ to $C_3$, or an aryl group;
  $R^1$, where
    $R^1$ represents a $C_1$ to $C_6$ alkyl group, preferably $C_1$ to $C_6$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; aryl, preferably phenyl; aralkyl, preferably benzyl; or heteroaryl;
  $S(O)_nR^2$, where
    n=0, 1 or 2,
    $R^2$ represents a $C_1$ to $C_6$ alkyl group, preferably $C_1$ to $C_4$; aryl, preferably phenyl or tolyl; aralkyl, preferably benzyl; or heteroaryl,
  $NR^3R^4$, where
    $R^3$ represents H; a $C_1$ to $C_6$ alkyl group, preferably $C_1$ to $C_4$; cycloalkyl, preferably cyclopropyl; aryl, preferably phenyl; aralkyl, preferably benzyl; or heteroaryl,
    R4 represents H; a $C_1$ to $C_6$ alkyl group, preferably $C_1$ to $C_4$; cycloalkyl, preferably cyclopropyl; aryl, preferably phenyl; aralkyl, preferably benzyl; heteroaryl; a $C_1$ to $C_6$ C(O)alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; a $C_1$ to $C_6$ $SO_2$-alkyl, preferably $C_1$ to $C_4$; $SO_2$-cycloalkyl, preferably cyclopropyl; $SO_2$-aryl, preferably phenyl; $SO_2$-heteroaryl; C(O)N$(R^5)_2$; where $R^5$ is as defined for $R^3$; $C(O)OR^6$, where $R^6$ represents a $C_1$ to $C_6$ alkyl group, preferably $C_1$ to $C_4$, alkyl group; or aralkyl, preferably benzyl; or $R^3$ and $R^4$ may be joined together to form a non-aromatic ring of 5 to 8 atoms or a 5- to 8-membered cyclic imide;
  $SR^5$, where
    $R^5$ represents a $C_1$ to $C_6$ alkyl group, preferably $C_1$ to $C_4$; preferably methyl; cycloalkyl, preferably cyclopropyl; aryl, preferably phenyl; aralkyl, preferably benzyl; or heteroaryl,
  $C(O)R^6$, where
    $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; $C_1$ to $C_6$ O-alkyl, preferably $C_1$ to $C_4$; O-cycloalkyl, preferably cyclopropyl; O-aryl, preferably phenyl; O-aralkyl, preferably benzyl; O-heteroaryl; or $N(R^7)(R^8)$;
    provided that when X represents $C(O)R^6$, then $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; or $N(R^7)(R^8)$;
    $R^7$ et $R^8$, which may be identical or different, represent H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl;
  $OR^7$, where
    $R^7$ represents H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; heteroaryl; a $C_1$ to $C_6$ C(O)-alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; $C_1$ to $C_6$ C(O)O-alkyl, preferably $C_1$ to $C_4$; C(O)O-cycloalkyl, preferably cyclopropyl; C(O)O-aryl, preferably phenyl; C(O)O-aralkyl, preferably benzyl; C(O)O-heteroaryl; $(CH_2)_mCCR^8$; $(CH_2)_pCH=CR^8$;
    where m=1 to 6 and p=1 to 6; or
  $CH_2OR^7$; $CH_2SR^5$; $CH_2NR^3R^4$; or $CH_2N_3$.

Advantageously, U represents Cl, and V, W, X and Y independently represent:
  H, provided that V, W, X and Y do not all simultaneously represent H;
  F, Cl, Br, CN or $N_3$;
  $Si(R^a)(R^b)(R^c)$, where
    $R^a$, $R^b$ and $R^c$, which may be identical or different, represent a $C_1$ to $C_6$ alkyl group, preferably $C_1$ to $C_3$, or an aryl group;
  $R^1$, where
    $R^1$ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$; $CF_2CF_3$ or $CH(CF_3)_2$; cycloalkyl, preferably cyclopropyl; aryl, preferably phenyl; aralkyl, preferably benzyl; or heteroaryl;
  $S(O)_nR^2$, where
    n=0, 1 or 2,
    $R^2$ represents a $C_1$ to $C_6$ alkyl group, preferably $C_1$ to $C_4$; aryl, preferably phenyl or tolyl; aralkyl, preferably benzyl; or heteroaryl,
  $NR^3R^4$, where
    $R^4$ represents H, $C_1$ to $C_6$ alkyl group, preferably $C_1$ to $C_4$; cycloalkyl, preferably cyclopropyl; aryl, preferably phenyl; aralkyl, preferably benzyl; heteroaryl;

$C_1$ to $C_6$ C(O)-alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; $C_1$ to $C_6$ $SO_2$-alkyl, preferably $C_1$ to $C_4$; $SO_2$-cycloalkyl, preferably cyclopropyl; $SO_2$-aryl, preferably phenyl; $SO_2$-heteroaryl; $C(O)N(R^5)_2$; where $R^5$ is as defined for $R^3$; $C(O)OR^6$, where $R^6$ represents a $C_1$ to $C_6$ alkyl group, preferably $C_1$ to $C_4$; or aralkyl, preferably benzyl; or $R^3$ and $R^4$ may be joined together to form a non-aromatic ring of 5 to 8 atoms or a 5- to 8-membered cyclic imide;

$SR^5$, where
  $R^5$ represents a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl, $C(O)R^6$, where
  $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; $C_1$ to $C_6$ O-alkyl, preferably $C_1$ to $C_4$; O-cycloalkyl, preferably cyclopropyl; O-aryl, preferably phenyl; O-aralkyl, preferably benzyl; O-heteroaryl; or $N(R^7)(R^8)$;
  provided that when X is $C(O)R^6$, then $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; or $N(R^7)(R^8)$;
    $R^7$ and $R^8$, which may be identical or different, represent H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl;

$OR^7$, where
  $R^7$ represents H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; heteroaryl; $C_1$ to $C_6$ C(O)-alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; $C_1$ to $C_6$ C(O)O-alkyl, preferably $C_1$ to $C^4$; C(O)O-cycloalkyl, preferably cyclopropyl; C(O)O-aryl, preferably phenyl; C(O)O-aralkyl, preferably benzyl; C(O)O-heteroaryl; $(CH_2)_mCCR^8$; $(CH_2)_pCH=CR^8$;
  Where m=1 to 6 and p=1 to 6; or
$CH_2OR^7$; $CH_2SR^5$; $CH_2NR^3R^4$; or $CH_2N_3$.

Advantageously, U represents Cl,
V, W and Y represent independently H, F, Cl, Br, CN or $N_3$, preferably H or Cl, and X represents:
H provided that V, W, X and Y do not all represent simultaneously H;
F, Cl, Br, CN or $N_3$;
$Si(R^a)(R^b)(R^c)$, where
  $R^a$, $R^b$ and $R^c$, which may be identical or different, represent a $C_1$ to $C_6$ alkyl group, preferably $C_1$ to $C_3$, or an aryl group;
$R^1$, where
  $R^1$ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; aryl, preferably phenyl; aralkyl, preferably benzyl; or heteroaryl;

$S(O)_nR^2$, where
  n=0, 1 or 2,
  $R^2$ represents a $C_1$ to $C_6$ alkyl group, preferably $C_1$ to $C_4$; aryl, preferably phenyl or tolyl; aralkyl, preferably benzyl; or heteroaryl, $NR^3R^4$, where
  $R^3$ represents H, a $C_1$ to $C_6$ alkyl group, preferably $C_1$ to $C_4$; cycloalkyl, preferably cyclopropyl; aryl, preferably phenyl; aralkyl, preferably benzyl; or heteroaryl,
  $R^4$ represents H; a $C_1$ to $C_6$ alkyl group, preferably $C_1$ to $C_4$; cycloalkyl, preferably cyclopropyl; aryl, preferably phenyl; aralkyl, preferably benzyl; heteroaryl; $C_1$ à $C_6$, C(O)-alkyl, preferably $C_1$ to $C_4$; (O)-cycloalkyl, preferably cyclopropyl; C(O)-aryl, preferably phenyl; C(O)-aralkyl, preferably benzyl; C(O)-heteroaryl; $C_1$ à $C_6$ $SO_2$-alkyl, preferably $C_1$ to $C_4$; $SO_2$-cycloalkyl, preferably cyclopropyl; $SO_2$-aryl, preferably phenyl; $SO_2$-heteroaryl; $C(O)N(R^5)_2$; where $R^5$ is as defined for $R^3$; $C(O)OR^6$, where $R^6$ represents a $C_1$ to $C_6$ alkyl group, preferably $C_1$ to $C_4$; or aralkyl, preferably benzyl; or $R^3$ and $R^4$ may be joined together to form a non-aromatic ring of 5 to 8 atoms or a 5- to 8-membered cyclic imide;

$SR^5$, where
  $R^5$ represents a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl, $C(O)R^6$, where
  $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; $C_1$ to $C_6$ O-alkyl, preferably $C_1$ to $C_4$; O-cycloalkyl, preferably cyclopropyl; O-aryl, preferably phenyl; O-aralkyl, preferably benzyl; O-heteroaryl; or $N(R^7)(R^8)$;
  provided that when X is $C(O)R^6$, then $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; or $N(R^7)(R^8)$;
    $R^7$ and $R^8$, which may be identical or different, represent H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl;

$OR^7$, where
  $R^7$ represents H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; heteroaryl; $C_1$ to $C_6$ C(O)-alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; $C_1$ to $C_6$ C(O)O-alkyl, preferably $C_1$ à $C_4$; C(O)O-cycloalkyl, preferably cyclopropyl; C(O)O-aryl, preferably phenyl; C(O)O-aralkyl, preferably benzyl; C(O)O-heteroaryl; $(CH_2)_mCCR^8$; $(CH_2)_pCH=CR^8$;
  Where m=1 to 6 and p=1 to 6; or
$CH_2OR^7$; $CH_2SR^5$; $CH_2NR^3R^4$; or $CH_2N_3$.

Advantageously, U represents Cl,
V, W and Y represent independently H, F, Cl, Br, CN or N3, preferably H or Cl, and X represents:

H, provided that V, W, X and Y do not all represent simultaneously H;

F; Cl; Br; or CN;

$R^1$, where
- $R^1$ advantageously represents, a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; or cycloalkyl, preferably cyclopropyl;
- $S(O)_nR^2$, where n=0, 1 or 2 and where $R^2$ advantageously represents a $C_1$ to $C_6$ alkyl group, preferably methyl;
- $C(O)R^6$, where $R^6$ represents a perfluorinated alkyl group, preferably trifluoromethyl; cycloalkyl, preferably cyclopropyl;
- $OR^7$, where $R^7$ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl;
- $NR^3R^4$; where $R^3$ represents a $C_1$ to $C_6$ alkyl group, preferably $C_1$ to $C_4$, cycloalkyl, preferably cyclopropyl, and $R^4$ represents a $C_1$ to $C_6$ alkyl group, preferably $C_1$ to $C_4$; cycloalkyl, preferably cyclopropyl; or $R^3$ and $R^4$ are joined together to form a non-aromatic ring of 5 to 8 atoms or a 5- to 8-membered cyclic imide; or
- $CH_2OR^7$ where $R^7$ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; $(CH_2)_mCCR^8$; $(CH_2)_pCH=CR^8$ where $R^8$ represents H, $Si(R^a)(R^b)(R^c)$, or $R^1$ and m=1 to 6 et p=1 to 6.

Even more preferably, U represents Cl, V, W and Y represent H or Cl, and X advantageously represents: H, F, Cl, Br, $CF_3$, CN, $SO_2CH_3$, $CH_3$, $CH_2CH_3$, cyclopropyl, C(O)cPr, $C(O)CF_3$, $Si(CH_3)_3$, $N(CH_3)_2$, or $CH_2OCH_2CCH$ provided that V, W, X and Y do not all simultaneously represent H.

Typically, U and V represent Cl, W and Y represent H, and X advantageously represents H, F, Cl, Br, $CF_3$, CN, $SO_2CH_3$, $CH_3$, $CH_2CH_3$, cyclopropyl, C(O)cPr, $C(O)CF_3$, $Si(CH_3)_3$, $N(CH_3)_2$, or $CH_2OCH_2CCH$, advantageously H.

Typically, U and W represent Cl, V and Y represent H, and X preferably represents H, F, Cl, Br, $CF_3$, CN, $SO_2CH_3$, $CH_3$, $CH_2CH_3$, cyclopropyl, C(O)cPr, $C(O)CF_3$, $Si(CH_3)_3$, $N(CH_3)_2$, or $CH_2OCH_2CCH$ advantageously H.

Typically, U and Y represent Cl, V and W represent H, and X represents preferably H, F, Cl, Br, $CF_3$, CN, $SO_2CH_3$, $CH_3$, $CH_2CH_3$, cyclopropyl, C(O)cPr, $C(O)CF_3$, $Si(CH_3)_3$, $N(CH_3)_2$, or $CH_2OCH_2CCH$ advantageously H.

According to a particular embodiment, U represents Cl, V, W and Y represent H, and X represents:

F, Cl, Br, CN, or $N_3$;

$Si(R^a)(R^b)(R^c)$, where
- $R^a$, $R^b$ and $R^c$, which may be identical or different, represent a $C_1$ to $C_6$ alkyl group, preferably $C_1$ to $C_3$, or an aryl group;

$R^1$, where
- $R^1$ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; aryl, preferably phenyl; aralkyl, preferably benzyl; or heteroaryl;

$S(O)_nR^2$, where
- n=0, 1 or 2,
- $R^2$ represents a $C_1$ to $C_6$ alkyl group, preferably $C_1$ to $C_4$; aryl, preferably phenyl or tolyl; aralkyl, preferably benzyl; or heteroaryl, $NR^3R^4$, where
- $R^3$ represents H, a $C_1$ to $C_6$ alkyl group, preferably $C_1$ to $C_4$; cycloalkyl, preferably cyclopropyl; aryl, preferably phenyl; aralkyl, preferably benzyl; or heteroaryl,
- $R^4$ represents H; a $C_1$ to $C_6$ alkyl group, preferably $C_1$ to $C_4$; cycloalkyl, preferably cyclopropyl; aryl, preferably phenyl; aralkyl, preferably benzyl; heteroaryl; $C_1$ to $C_6$ C(O)-alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; $C_1$ to $C_6$ $SO_2$-alkyl, preferably $C_1$ to $C_4$; $SO_2$-cycloalkyl, preferably cyclopropyl; $SO_2$-aryl, preferably phenyl; $SO_2$-heteroaryl; $C(O)N(R^5)_2$; where $R^5$ is as defined for $R^3$; C(O)OR$^6$, where $R^6$ represents $C_1$ to $C_6$ alkyl group, preferably $C_1$ to $C_4$; or aralkyl, preferably benzyl; or $R^3$ and $R^4$ may be joined together to form a non-aromatic ring of 5 to 8 atoms or a 5- to 8-membered cyclic imide;

$SR^5$, where
- $R^5$ represents a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl, $C(O)R^6$, where
- $R^6$ represents a $C_1$ to $C_6$ alkyl group, preferably $C_1$ to $C_4$, preferably methyl; perfluorinated alkyl, preferably trifluoromethyl; cycloalkyl, preferably cyclopropyl; aryl, preferably phenyl; aralkyl, preferably benzyl; heteroaryl; or $N(R^7)(R^8)$,
- $R^7$ and $R^8$, which may be identical or different, represent H; a $C_1$ to $C_6$ alkyl group, preferably $C_1$ to $C_4$, preferably methyl; cycloalkyl, preferably cyclopropyl; aryl, preferably phenyl; aralkyl, preferably benzyl; or heteroaryl;

$OR^7$, where
- $R^7$ represents H; a $C_1$ to $C_6$ alkyl group, preferably $C_1$ to $C_4$ group, preferably methyl; cycloalkyl, preferably cyclopropyl; aryl, preferably phenyl; aralkyl, preferably benzyl; heteroaryl; $C_1$ to $C_6$ C(O)-alkyl, preferably $C_1$ to $C_4$; C(O)-cycloalkyl, preferably cyclopropyl; C(O)-aryl, preferably phenyl; C(O)-aralkyl, preferably benzyl; C(O)-heteroaryl; $C_1$ to $C_6$ C(O)O-alkyl, preferably $C_1$ to $C_4$; C(O)O-cycloalkyl, preferably cyclopropyl; C(O)O-aryl, preferably phenyl; C(O)O-aralkyl, preferably benzyl; C(O)O-heteroaryl; $(CH_2)_mCCR^8$; $(CH_2)_pCH=CR^8$;
- Where m=1 to 6 and p=1 to 6; or $CH_2OR^7$; $CH_2SR^5$; $CH_2NR^3R^4$; or $CH_2N_3$.

Advantageously, U represents Cl, V, W and Y represent H, and X represents advantageously F; Cl; Br; or CN;

$R^1$, where
- $R^1$ advantageously represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; or cycloalkyl, preferably cyclopropyl;

$S(O)_nR^2$, where n=0, 1 or 2 and where $R^2$ advantageously represents a $C_1$ to $C_6$ alkyl group, preferably methyl;

C(O)R⁶, where R⁶ represents a perfluorinated alkyl group, preferably trifluoromethyl; cycloalkyl, preferably cyclopropyl;

OR⁷, where R⁷ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl;

NR³R⁴; where R³ represents a $C_1$ to $C_6$ alkyl group, preferably $C_1$ to $C_4$; cycloalkyl, preferably cyclopropyl, and R⁴ represents a $C_1$ to $C_6$ alkyl group, preferably $C_1$ to $C_4$; cycloalkyl, preferably cyclopropyl; or R³ and R⁴ are joined together to form a non-aromatic ring of 5 to 8 atoms or a 5- to 8-membered cyclic imide; or CH₂OR⁷ where R⁷ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; $(CH_2)_mCCR^8$; $(CH_2)_pCH=CR^8$ where R⁸ represents H, $Si(R^a)(R^b)(R^c)$, or R¹ and m=1 to 6 et p=1 to 6.

Even more advantageously, U represents Cl, V, W and Y represent H, and X advantageously represents:

F; Cl; Br; CN;

R¹, preferably a $C_1$ to $C_6$ alkyl group, preferably $C_1$ to $C_4$, or a $C_2$ to $C_6$ alkyl group, preferably $C_2$ to $C_4$, a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl;

$S(O)_nR^2$, where n=0, 1 or 2 and where R² advantageously represents a $C_1$ to $C_6$ alkyl group, preferably methyl;

C(O)R⁶, where R6 represents a perfluorinated alkyl group, preferably trifluoromethyl; cycloalkyl, preferably cyclopropyl;

OR⁷, where R⁷ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl;

NR³R⁴ where R³ represents a $C_1$ to $C_6$ alkyl group, preferably $C_1$ to $C_4$; cycloalkyl, preferably cyclopropyl, and R⁴ represents a $C_1$ to $C_6$ alkyl group, preferably $C_1$ to $C_4$; cycloalkyl, preferably cyclopropyl; or R³ and R⁴ are joined together to form a non-aromatic ring of 5 to 8 atoms or a 5- to 8-membered cyclic imide; or CH₂OR⁷ where R⁷ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; $(CH_2)_mCCR^8$; $(CH_2)_pCH=CR^8$ where R⁸ represents H, $Si(R^a)(R^b)(R^c)$, or R¹ and m=1 to 6 and p=1 to 6.

Even more advantageously, U represents Cl, V, W and Y represent H, and X represents advantageously: F, Cl, Br, $CF_3$, CN, $SO_2CH_3$, $CH_3$, $CH_2CH_3$, cyclopropyl, C(O)cPr, C(O)CF₃, Si(CH₃)₃, N(CH₃)₂, or CH₂OCH₂CCH.

According to a particular characteristic of the invention, in the compound of formula (I), U represents Cl, V, W and Y represent H, and X represents F, Cl, Br, $CF_3$, CN, $SO_2CH_3$, $CH_2CH_3$, cyclopropyl, C(O)cPr, C(O)CF₃, Si(CH₃)₃, N(CH₃)₂, or CH₂OCH₂CCH.

According to another particular embodiment of the invention, in the compound of formula (I), U represents Cl, V, W and Y represent H, and X represents:

Cl; Br or CN;

R¹, advantageously a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl;

C(O)R⁶, where R⁶ represents a perfluorinated alkyl group, preferably trifluoromethyl; cycloalkyl, preferably cyclopropyl;

CH₂OR⁷ where R⁷ represents a $C_1$ to $C_6$ alkyl group, preferably $C_1$ to $C_4$, preferably methyl; a $C_1$ to $C_6$ perfluoroalkyl group, preferably $C_1$ to $C_4$, preferably $CF_3$, $CF_2CF_3$ or $CH(CF_3)_2$; cycloalkyl, preferably cyclopropyl; $(CH_2)_pCH=CR^8$ where R⁸ represents H, $Si(R^a)(R^b)(R^c)$, or R1 and m=1 to 6 and p=1 to 6.

More advantageously, in the compound of formula (I), U represents Cl, V, W and Y represent H, and X represents Cl, Br, $CF_3$, CN, C(O)cPr, C(O)CF₃, or CH₂OCH₂CCH.

Particularly advantageously, in the compound of formula (I), U represents Cl, V, W and Y represent H, and X represents Cl.

According to another particular embodiment of the invention, in the compound of formula (I), U represents Cl, X, W and Y represent H, and V represents Cl.

According to another particular embodiment of the invention, in the compound of formula (I), U represents Cl, X, V and Y represent H, and W represents Cl.

According to another particular embodiment of the invention, in the compound of formula (I), U represents Cl, X, V and W represent H, and Y represents Cl.

According to another particular embodiment of the invention, the compound of formula (I) is chosen from the compounds mentioned in table 1 with the exception of HCQ and NT36F9 and/or the compound of formula (I) is selected from the compounds listed in Table 2, with the exception of HCQ.

Advantageously, the compound of formula (I) is in enantiomerically pure form, that is to say an optical purity greater than 95%, preferably greater than 98%. Preferably, it is the (R) enantiomer.

The present invention also relates to a compound of formula (I) as defined above for its use as a drug.

The present invention advantageously relates to a compound of formula (I) as defined above for its use as an anti-inflammatory agent, preferably for its use in the treatment of lupus erythematosus, preferably for use in the treatment of systemic lupus erythematosus.

The present invention also relates to a compound of formula (I) as defined above for its use in the treatment of vasculitis.

The present invention is particularly suitable for use in the treatment of rheumatoid arthritis.

The compounds of formula (I) possess properties of inhibition of autophagy. The present invention therefore also relates to a compound of formula (I) for its use in the treatment of cancer in association with an anti-cancer agent, in particular lung cancer or colorectal cancer.

Definitions:

In the present invention, the term "pharmaceutically acceptable" is intended to mean that which is useful in the preparation of a pharmaceutical composition which is generally safe, nontoxic and neither biologically nor otherwise undesirable and is acceptable for veterinary as well as human pharmaceutical use.

"Pharmaceutically acceptable salts" of a compound is intended to mean salts which are pharmaceutically acceptable, as defined herein, and which possess the desired pharmacological activity of the parent compound. Such salts include:

(1) hydrates and solvates, (2) pharmaceutically acceptable acid addition salts formed with pharmaceutically acceptable inorganic acids such as hydrochloric acid, hydrobromic acid, sulfuric acid, nitric acid, phosphoric acid and the like; or formed with pharmaceutically acceptable organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and the like, or (3) pharmaceutically acceptable base addition salts formed when an acid proton present in the parent compound is either replaced by a metal ion, for example, an alkali metal ion, an alkaline earth metal ion or an aluminum ion; is coordinated with a pharmaceutically acceptable organic or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

For the purposes of the present invention, the term "$C_1$ to $C_6$ alkyl" is understood to mean a saturated, linear or branched, monovalent hydrocarbon chain containing 1 to 6, preferably 1 to 4, carbon atoms. Mention may be made, for example, of methyl, ethyl, propyl, isopropyl, butyl, isobutyl, sec-butyl, tert-butyl, pentyl or hexyl groups.

The $C_1$ to $C_6$ alkyl group may optionally be substituted by one or more halogen atoms, in particular fluorine atoms. It may in particular be a $CF_3$ group.

For the purposes of the present invention, the term "$C_3$ to $C_6$ cycloalkyl" is understood to mean a cyclic saturated hydrocarbon chain containing 3 to 6 ring carbon atoms. By way of example, mention may be made of cyclopropyl, cyclopentyl and cyclohexyl.

For the purposes of the present invention, "aryl" is understood to mean an aromatic hydrocarbon group, preferably containing from 6 to 10 carbon atoms, and comprising one or more attached rings, such as, for example, a phenyl or naphthyl group. Advantageously, it is phenyl. The aryl may optionally be substituted with one or more groups chosen, for example, from alkyl or O-alkyl groups comprising 1 to 4 carbon atoms, such as methyl, ethyl, propyl or butyl, halogens such as F, or Cl, perfluoroalkyls such as $CF_3$, $NO_2$ or CN.

For the purposes of the present invention, "heteroaryl" is understood to mean an aromatic group comprising 5 to 10 ring atoms of which one or more heteroatoms, advantageously 1 to 4 and even more preferably 1 or 2, such as, for example, sulfur atoms, nitrogen or oxygen, the other ring atoms being carbon atoms. Examples of heteroaryl groups are furyl, thienyl, pyrrolyl, pyridinyl, pyrimidinyl, pyrazolyl, imidazolyl, triazolyl, tetrazolyl or indyl. The heteroaryl may optionally be substituted with one or more groups chosen, for example, from alkyl or O-alkyl groups comprising 1 to 4 carbon atoms, such as methyl, ethyl, propyl or butyl, halogens such as F or Cl, $NO_2$ or CN.

For the purposes of the present invention, "perfluoroalkyl" is understood to mean an alkyl chain as defined above in which one or more hydrogen atoms are replaced by fluorine atoms. Mention may be made, by way of example, of the groups $CF_3$, $CH_2CF_3$ or $CH(CF_3)_2$.

For the purposes of the present invention, the term "non-aromatic ring of 5 to 8 atoms" is understood to mean a saturated or unsaturated but non-aromatic 5 to 8-membered ring containing one or more, advantageously 1 to 4, even more preferably 1 or 2, heteroatoms, such as, for example, sulfur, nitrogen or oxygen atoms. They may in particular be the pyrrolidinyl, piperidinyl, piperazinyl or morpholinyl group. The non-aromatic ring of 5 to 8 atoms may optionally be substituted with one or more groups chosen, for example, from alkyl or O-alkyl groups comprising 1 to 4 carbon atoms, such as methyl, ethyl, propyl or butyl, Such as F, or Cl or perfluoroalkyls such as $CF_3$, $NO_2$ or CN.

Examples of "5 to 8-membered cyclic imide" are, for example, a succinimide or phthalimide group.

For the purposes of the present invention, "aralkyl" is understood to mean an aryl group, as defined above, joined to the molecule via a ($C_1$-$C_6$) alkyl chain, as defined above. By way of example, mention may be made of the benzyl group.

Pharmaceutical Composition:

The present invention also relates to a pharmaceutical composition comprising at least one compound of formula (I) as defined above.

The pharmaceutical composition according to the invention can be formulated for oral or sublingual administration, intended for mammals, including humans.

The active ingredient may be administered in unit dosage forms, in admixture with conventional pharmaceutical carriers, to animals or to humans. Suitable unit forms of administration include oral forms such as tablets, capsules, powders, granules and oral solutions or suspensions, and forms of sublingual and buccal administration.

The compounds of the invention as active ingredients may be used in doses of between 0.01 mg and 1000 mg per day, given in a single dose once a day or administered in several doses throughout the day, for example twice a day in equal doses. The dose administered per day is advantageously comprised between 5 mg and 500 mg, even more advantageously between 10 mg and 200 mg. The dosage varies according to the treatment and the condition in question and can be determined by those skilled in the art.

Use of the Compounds:

The present invention further relates to compounds of formula (I'), pharmaceutically acceptable salts, solvates or hydrates thereof, in the form of an enantiomer or a mixture of enantiomers:

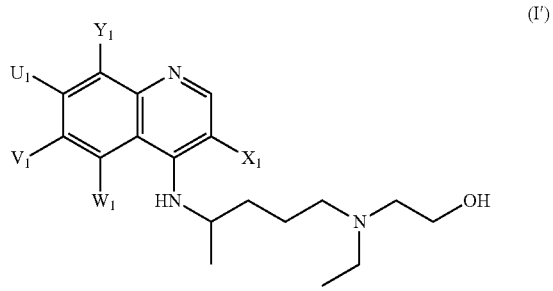

(I')

in which $U_1$ represents:
F, Cl, Br, CN, $CF_3$, or $N_3$;
And $V_1$, $W_1$, $X_1$ and $Y_1$ independently represent I, $NO_2$ or H, provided that $V_1$, $W_1$, $X_1$ and $Y_1$ do not all simultaneously represent H, for its use as an anti-inflammatory agent, advantageously for its use in the treatment of lupus erythematosus, more preferably in the treatment of systemic lupus erythematosus.

Advantageously, in the compound of formula (I'), $U_1$ represents Cl, $V_1$, $W_1$, and $Y_1$ represent H, and $X_1$ represents I or $NO_2$, for its use as an anti-inflammatory agent, advantageously for its use in the treatment of lupus erythematosus, more preferably in the treatment of systemic lupus erythematosus.

The present invention also relates to compounds of formula (I") its pharmaceutically acceptable salt, solvate or hydrate, in the form of an enantiomer or a mixture of enantiomers:

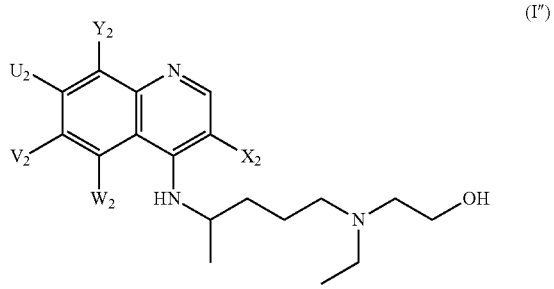

(I")

in which $U_2$ represents:
F, Cl, Br, CN, $CF_3$, or $N_3$;
and $V_2$, $W_2$, $X_2$ and $Y_2$ independently represent H, with the proviso that $V_2$, $W_2$, $X_2$ and $Y_2$ do not all represent simultaneously H, or $C(O)R^6$, where $R^6$ represents $C_1$ to $C_6$ O-alkyl, preferably $C_1$ to $C_4$; O-cycloalkyl, preferably cyclopropyl; O-aryl, preferably phenyl; O-aralkyl, preferably benzyl; or O-heteroaryl; for its use in the treatment of lupus erythematosus, more preferably in the treatment of systemic lupus erythematosus.

Advantageously, in the compound of formula (I") $U_2$ represents Cl, $V_2$, $W_2$, and $Y_2$ represent H, and $X_2$ represents $C(O)R^6$, where $R^6$ represents $C_1$ to $C_6$ O-alkyl, preferably $C_1$ to $C_4$; O-cycloalkyl, preferably cyclopropyl; O-aryl, preferably phenyl; O-aralkyl, preferably benzyl; or O-heteroaryl; for its use in the treatment of lupus erythematosus, more preferably in the treatment of systemic lupus erythematosus.

Advantageously, in the compound of formula (I") $U_2$ represents Cl, $V_2$, $W_2$, and $Y_2$ represent H, and $X_2$ represents $C(O)R^6$, where $R^6$ represents $C_1$ to $C_6$ O-alkyl, preferably $C_1$ to $C_4$ for its use in the treatment of lupus erythematosus, more preferably in the treatment of systemic lupus erythematosus.

Advantageously, the compounds of formula (I') or (I") are in enantiomerically pure form, that is to say an optical purity greater than 95%, preferably greater than 98%. Preferably, it is the (R)-enantiomer.

The present invention relates to compounds of formula (I') or (I"), as defined above, for their use in the treatment of various autoimmune or inflammatory diseases, in particular in the treatment of systemic lupus erythematosus, rheumatoid arthritis, other forms of polyarthritis, antiphospholipid syndrome, skin expression vasculitis, or for use in the treatment of vasculitis, including the presence of anti-neutrophil cytoplasmic antibodies (ANCA), in particular anti-myeloperoxidase antibodies (anti-MPO).

The present invention also relates to compounds of formula (I') or (I"), as defined above, for their use in the treatment of various disorders such as allergic diseases (in particular asthma, allergic rhinitis) diseases Autoimmune diseases (including multiple sclerosis, rheumatoid arthritis, Crohn's disease, psoriasis), degenerative diseases (including Alzheimer's disease, AMD, chronic degenerative arthropathy); metabolic diseases (including non-alcoholic steatohepatitis, type II diabetes, metabolic syndrome, atherosclerosis, cardiac disease, hypertension), chronic infections (including HIV infection, HCV, HBV, CMV, tuberculosis or any other viral or bacterial infections).

The present invention also relates to compounds of formula (I') or (I"), as defined above, for their use in the treatment of various inflammatory diseases in association with an anti-inflammatory agent, especially in the treatment of lupus erythematosus.

The present invention also relates to compounds of formula (I') or (I"), as defined above, for their use in the treatment of cancer such as colon, breast, brain and bone cancer (including osteosarcoma, chondrosarcoma, neuroblastoma, adenocarcinoma of the colon), leukemias, heart cancers (including sarcoma, myxoma, rhabdomyoma), lung (including bronchial carcinoma, alveolar carcinoma, sarcoma, lymphoma), gastrointestinal cancer (including osteosarcoma, chondrosarcoma, neuroblastoma, adenocarcinoma of the colon), gastro-intestinal cancer (including cancer of the esophagus, stomach, pancreas, intestine), urogenital cancer (including kidney, urethra, prostate, testes, liver cancer), genital cancer (including Hodgkin's disease, non-Hodgkin's lymphoma), and skin cancer (including melanoma, squamous cell carcinoma, basal cell carcinoma, squamous cell carcinoma, lipoma, angioma).

The present invention also relates to compounds of formula (I') or (I"), as defined above, for their use in the treatment of cancer in association with an anti-cancer agent, in particular in the treatment of lung cancer or colorectal cancer.

The compounds of formula (I), (I') or (I") may also be used as tracers or probes for imaging. The present invention therefore also relates to the use of a compound of formula (I), (I') or (I") as a tracer or probe for imaging. The compounds are advantageously used in the field of proteomics or as a fluorescent probe.

Advantageously, the compounds of formula (I), (I') or (I") used in imaging are those containing an alkyne or azide $N_3$ function.

Preparation of the Compounds:

The inventors have also developed a new synthetic method using 4-hydroxy-7-chloroquinoline (CAS 86-99-7) as reagent according to the following reaction scheme:

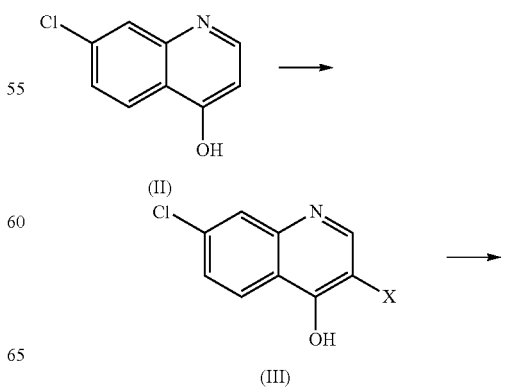

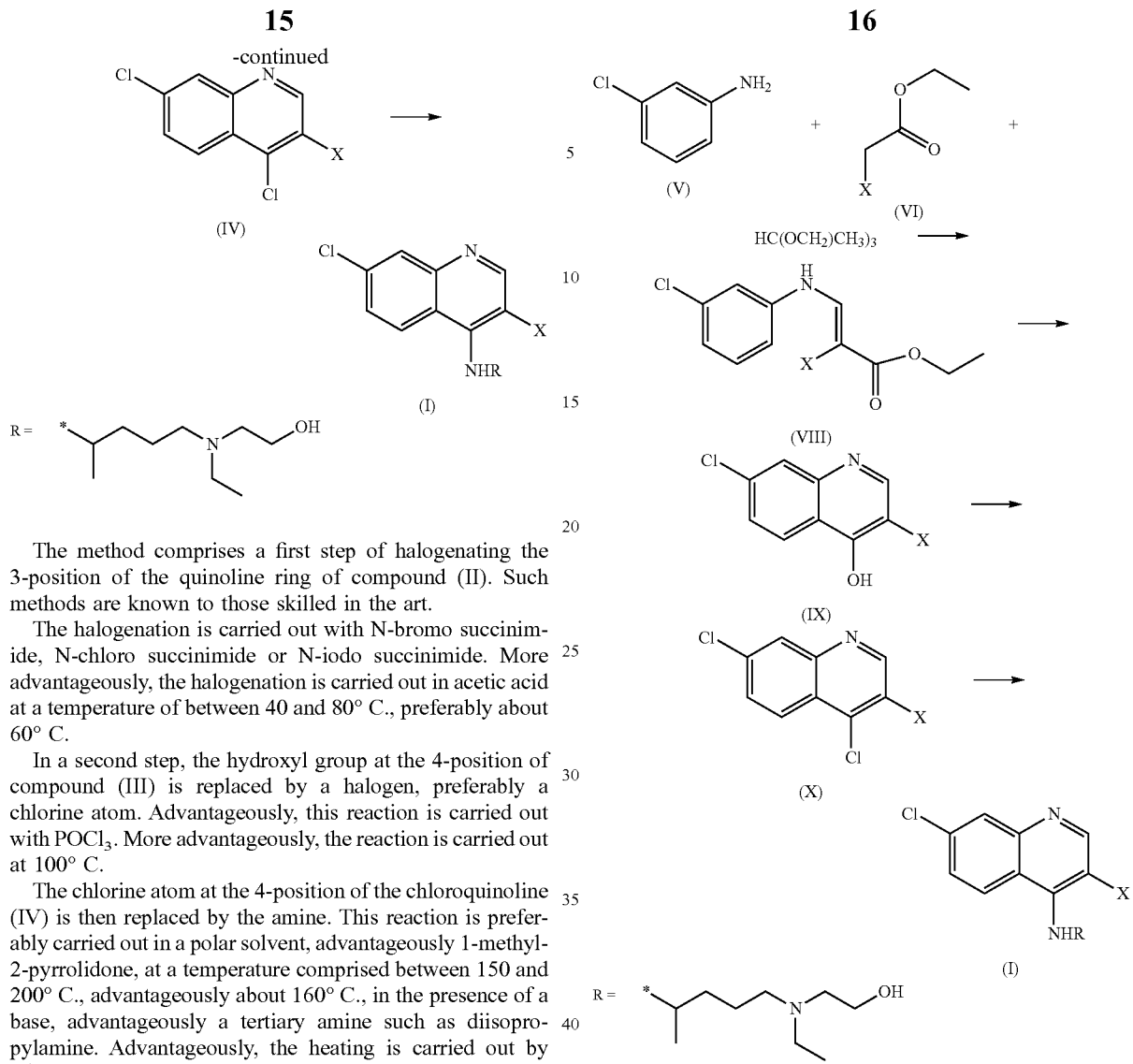

The method comprises a first step of halogenating the 3-position of the quinoline ring of compound (II). Such methods are known to those skilled in the art.

The halogenation is carried out with N-bromo succinimide, N-chloro succinimide or N-iodo succinimide. More advantageously, the halogenation is carried out in acetic acid at a temperature of between 40 and 80° C., preferably about 60° C.

In a second step, the hydroxyl group at the 4-position of compound (III) is replaced by a halogen, preferably a chlorine atom. Advantageously, this reaction is carried out with $POCl_3$. More advantageously, the reaction is carried out at 100° C.

The chlorine atom at the 4-position of the chloroquinoline (IV) is then replaced by the amine. This reaction is preferably carried out in a polar solvent, advantageously 1-methyl-2-pyrrolidone, at a temperature comprised between 150 and 200° C., advantageously about 160° C., in the presence of a base, advantageously a tertiary amine such as diisopropylamine. Advantageously, the heating is carried out by microwaves.

The optionally protected halogenated intermediate (IV) may then be used for obtaining some of the compounds of formula (I) using methods conventional to the person skilled in the art. A $R^1$ group, such as aryl or alkyl, may for example be introduced by a Suzuki reaction with an arylboronic acid or the Kumada reaction with a Grignard reagent. Perfluoroalkyl groups such as $CF_3$ can be introduced by a reaction catalyzed by copper. For example, the compound where $X=CF_3$ is introduced by a reaction between the iodinated quinoline of formula (IV) by reaction with (phen) $CuCF_3$, in a polar solvent such as DMF at a temperature of about 80° C.

It is the addition of the aromatic chain R, as defined in the above reaction scheme in the last step of synthesis of the compounds of the present invention from the compound of formula (IV), which makes it possible to obtain a racemic mixture or a mixture in enantiomerically pure form. Preferably, it is the (R)-enantiomer.

An $OR^7$ group; $SR^5$ or $NR^3R^4$ may be introduced by reaction of the derivative with the corresponding alcohol, sulfide or amine, optionally in the presence of a transition metal as a catalyst or thermally in the presence of a base.

Compounds of formula (I) in which X represents $S(O)_nR^2$, CN or $CO(R^6)$ can be prepared according to the following reaction scheme:

In a first step, the compounds (V), (VI) and (VII) are reacted at a temperature between 110 and 150° C., advantageously about 130° C.

The cyclization of the compound (VIII) to the compound (IX) is then carried out in an aromatic solvent at a temperature of between 200 and 280° C., advantageously approximately 250° C. Advantageously, the solvent is a mixture of biphenyl ($C_{12}H_{10}$) and diphenyloxide ($C_{12}H_{10}O$), sold under the trade name Dowtherm®.

The hydroxyl group of the compound (IX) is then replaced by a halogen, preferably a chlorine atom. Advantageously, this reaction is carried out with $POCl_3$. More advantageously, the reaction is carried out at 100° C. for 2 hours.

The chlorine atom at position 4 of the chloroquinoline (IV) is then replaced by the amine. This reaction is preferably carried out in a polar solvent, advantageously dimethyl sulphoxide, at a temperature of between 150 and 200° C., advantageously about 160° C., in the presence of a base, advantageously a tertiary amine such as diisopropylamine. Advantageously, the heating is carried out by microwaves.

The preparation of the compounds of formula (I) in which $X=C(O)R^6$ may also be carried out starting from 4,7- dichloroquinoline (IV) according to the reaction scheme below, illustrating the preparation of the compound in which $R^6$=$CF_3$:

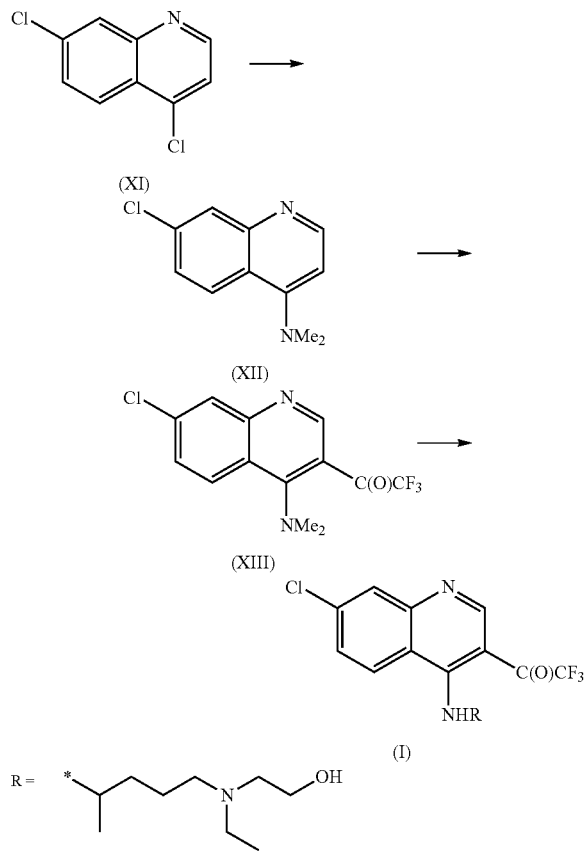

In a first step, the chlorine atom of the compound (XI) is substituted by an $N(CH_3)_2$ group. The reaction is preferably carried out in a polar solvent, advantageously acetonitrile, at a temperature of between 40 and 60° C., advantageously 50° C.

The compound obtained in the first step (XII) is then reacted with an acyl chloride or an anhydride of formula $R^6C(O)OC(O)R^6$. The reaction is advantageously carried out in the presence of a catalyst, for example 4-dimethylaminopyridine (DMAP) in an apolar solvent, advantageously xylene, at a temperature of between 100 and 180° C., advantageously about 150° C.

In a third step, the amine group in position 4 of the compound of formula (XIII) is substituted by the amine of HCQ. The reaction is carried out in a polar solvent, advantageously acetonitrile, at a temperature of between 60 and 90° C., advantageously at approximately 80° C.

Screening Method:

In another embodiment, the present invention relates to a method of identifying a compound useful for the treatment of lupus erythematosus, advantageously systemic lupus erythematosus, or the treatment of cancer, and free from retinal toxicity comprising the steps of:
  a) selecting a test compound inhibiting MPO,
  b) determining the $K_A$ association constant of the test compound with αB-crystalline, and
  c) selecting the test compound having no affinity for αB-crystalline.

The selection of the inhibitory compounds of MPO according to step (a) is carried out according to a method comprising the steps of:
  (a1) contacting a test compound with MPO,
  (a2) determining the activity of MPO in the presence of this test compound,
  (a3) comparing the activity of MPO in the presence of this test compound with that of MPO in the absence of this test compound, and
  (a4) selecting the test compound that reduces the activity of MPO.

The activity of MPO is measured by methods well known to those skilled in the art, in particular those presented in the examples of the present application.

The determination of the $K_A$ association constant of the test compound with the αB-crystalline of step (b) is carried out according to a method comprising the steps of:
  (b1) contacting a test compound with the αB-crystalline protein,
  (b2) determining the $K_A$ association constant of the test compound with αB-crystalline, and
  (b3) selecting the test compound having no affinity for αB-crystalline.

For the purposes of the present invention, a compound not interacting with αB-crystalline is defined as a compound whose $K_A$ association constant is equal to 0.

For the purposes of the present invention, "test compound" is understood to mean compounds of different natures and origins, in particular synthetic chemical compounds, which are tested for their ability to inhibit MPO and/or their affinity for αB-crystalline.

EXAMPLES

Syntheses of the Compounds According to the Invention:
1) A Compound of Formula (I) Where X=CN To a suspension of 4,7-dichloroquinoline-3-carbonitrile (53 mg, 0.23 mmol) in 1.2 mL of N,N-dimethylformamide is added 2-[(4-aminopentyl)(ethyl)amino]ethan-1-ol (124 mg, 0.71 mmol) and triethylamine (0.12 mL, 0.71 mmol). The reaction medium is irradiated with microwaves for 20 min at 180° C. and then diluted in ethyl acetate and washed three times with a saturated NaCl solution. The organic phase is dried over $MgSO_4$, filtered and concentrated and then purified on a silica column with a 10/0 to 80/20 dichloromethane/methanol gradient.

Yield 57%. Colorless oil; RMN $^1$H (DMSO, 400 MHz) δ 1.17 (3H, t, J=7.2 Hz); 1.38 (3H, d, J=6.4 Hz); 1.64-1.87 (m, 4H); 3.08-3.18 (m, 6H); 3.69 (2H, dt, J=5.1, 1.5 Hz); 4.62 (1H, m); 7.71 (1H, dd, J=9.1. 2.3 Hz); 7.90 (1H, d, J=2.2 Hz); 8.18 (1H, dl, J=8.1 Hz). 8.59 (1H, d, J=9.1 Hz); 8.69 (s, 1H); 9.14 (sl, 1H). RMN $^{13}$C (DMSO, 100 MHz): 8.3; 19.8; 20.9; 32.9; 47.5; 49.8; 51.5; 53.3; 55.1; 82.6; 116.8; 119.1; 125.1; 126.2; 137.0; 146.5; 151.9; 154.0.

HRMS calculated for $C_{19}H_{25}ClN_4O$: 360.1707; Mass found: 360.1717

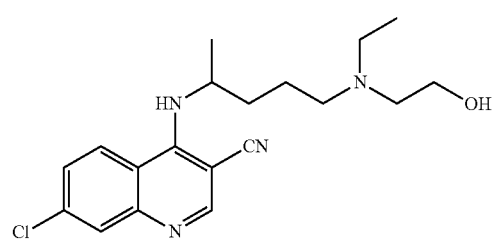

2) A Compound of Formula (I) Where X=Cl

N-chlorosuccinimide (408 mg, 3.06 mmol) is added to a suspension of 7-chloroquinolin-4-ol (500 mg, 2.78 mmol) in 20 mL of acetic acid. The reaction is heated at 60° C. for 5 hours and then diluted in water and filtered. The white solid is washed with water and dried under vacuum.

Yield 88%. White solid; RMN ¹H (DMSO, 400 MHz) δ 7.40 (1H, dd, J=8.8. 2.0 Hz), 7.64 (1H, d, J=2.0 Hz), 8.14 (1H, d, J=8.8 Hz), 8.45 (1H, s), 12.24 (1H, sl); RMN ¹³C (DMSO, 100 MHz) δ 170.6; 139.9; 138.5; 136.5; 127.5; 124.2; 123.2; 117.7; 114.7.

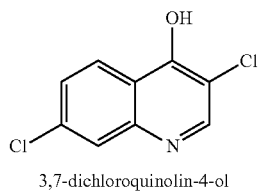 [SMILES: Oc1c(Cl)cnc2cc(Cl)ccc12]

3,7-dichloroquinolin-4-ol

A suspension of 3,7-dichloroquinolin-4-ol (500 mg, 2.33 mmol) in 6.5 mL of phosphoryl trichloride is heated at 100° C. for 2 hours. Once at room temperature, the solution is poured into a water/ice mixture, filtered and washed with a saturated NaHCO₃ solution and then water. The resulting white solid is dried and used without further purification.

Yield 92%. White solid; RMN ¹H (DMSO, 400 MHz) δ 7.88 (1H, dd, J=9.1, 2.2 Hz); 8.24 (1H, d, J=2.2 Hz); 8.26 (1H, d, J=9.1 Hz); 9.07 (1H, s); RMN ¹³C (DMSO, 100 MHz) δ 124.8; 126.0; 127.0; 128.3; 129.7; 135.5; 138.3; 146.7; 151.0. SM (ESI⁺): m/z=232 [M+1].

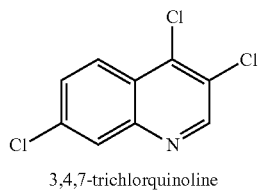 [SMILES: Clc1ccc2c(Cl)c(Cl)cnc2c1]

3,4,7-trichlorquinoline

2-[(4-aminopentyl) (ethyl) amino] ethan-1-ol (750 mg, 4.3 mmol) is added to a suspension of 3,4,7-trichloroquinoline (500 mg, 2.15 mmol) in 5 mL of N-methyl-2-pyrrolidone and triethylamine (0.6 mL, 4.3 mmol). The reaction medium is irradiated with microwaves for 20 min at 160° C. and then diluted in ethyl acetate and washed three times with a saturated NaCl solution. The organic phase is dried over MgSO₄, filtered and concentrated and then purified on a silica column with a 10/0 to 80/20 dichloromethane/methanol gradient.

Yield 85%. Colorless oil; RMN ¹H (DMSO, 400 MHz) δ 0.83 (3H, t, J=7.2 Hz); 1.26 (3H, d, J=6.4 Hz); 1.34-1.69 (4H, m); 2.29-2.38 (6H, m); 3.35 (1H, m); 4.21-4.31 (2H, m); 6.06 (1H, d, J=9.5 Hz); 7.57 (1H, dd, J=9.1, 2.3 Hz); 7.88 (1H, d, J=2.3 Hz); 8.35 (1H, d, J=9.2 Hz); 8.49 (1H, s). RMN ¹³C (DMSO, 100 MHz) δ 11.4; 21.8; 23.3; 35.2; 47.4; 51.7; 53.0; 55.3; 58.9; 111.2; 120.2; 124.9; 125.6; 127.7; 133.7; 147.1; 147.7; 151.8.

HRMS calculated for $C_{18}H_{25}Cl_2N_3O$: 369.1369; mass found: 369.1375

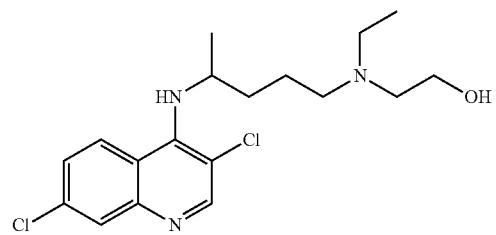 [SMILES: CCN(CCO)CCCC(C)Nc1c(Cl)cnc2cc(Cl)ccc12]

3) A Compound of Formula (I) Where X=I

N-iodosuccinimide (626 mg, 2.78 mmol) was added to a suspension of 7-chloroquinolin-4-ol (500 mg, 2.78 mmol) in 16 mL of acetic acid. The reaction is heated at 60° C. for 5 hours and then diluted in water and filtered. The white solid is washed with water and dried under vacuum.

Yield 87%. White solid; RMN ¹H (DMSO, 400 MHz) δ 7.39 (1H, dd, J=8.8, 2.2 Hz); 7.62 (1H, d, J=2.2 Hz); 8.10 (1H, d, J=8.8 Hz); 8.55 (s, 1H); 12.21 (sl, 1H); RMN ¹³C (DMSO, 100 MHz) δ 81.3; 117.6; 120.9; 124.4; 127.3; 140.3; 145.3; 172.5. SM (ESI⁺): m/z=523 [M+1]

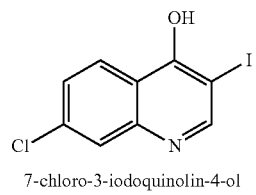 [SMILES: Oc1c(I)cnc2cc(Cl)ccc12]

7-chloro-3-iodoquinolin-4-ol

A suspension of 7-chloro-3-iodoquinolin-4-ol (500 mg, 1.64 mmol) in 4.5 mL of phosphoryl trichloride is heated at 100° C. for 2 hours. Once at room temperature, the solution is poured into a water/ice mixture, filtered and washed with a saturated NaHCO₃ solution and then water. The resulting white solid is dried and used without further purification.

Yield 48%. White solid; RMN ¹H (DMSO, 400 MHz) δ 7.78 (1H, dd, J=9.1, 2.2 Hz); 8.15 (1H, d, J=2.2 Hz); 8.23 (1H, d, J=9.1 Hz); 9.18 (s, 1H); RMN ¹³C (DMSO, 100 MHz) δ 97.2; 125.2; 126.5; 128.1; 129.5; 144.9; 147.3; 158.0. SM (ESI⁺): m/z=523 [M+1]

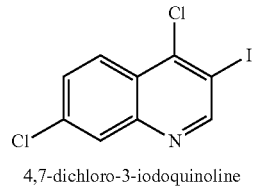 [SMILES: Clc1ccc2c(Cl)c(I)cnc2c1]

4,7-dichloro-3-iodoquinoline (Phen)CuCF₃ (62.8 mg, 0.201 mmol) is added to a solution of 4,7-dichloro-3-iodoquinoline (50 mg, 0.154 mmol) in 1.5 mL of DMF. After one night at 50° C., 1 eq. of (Phen)CuCF₃ is added and the reaction is continued for 6 hours at 80° C. The reaction medium is diluted in ether and filtered through Celite®. The filtrate is successively washed with a solution of HCl 1M, NaHCO₃ and NaCl. The organic phase is dried over MgSO₄, filtered and concentrated. The crude is purified on a silica column with a 10/0 to 50/50 cyclohexane/EtOAc gradient.

Yield 83%. White solid; SM (ESI⁺): m/z=266 [M+1]

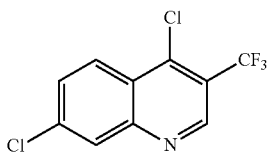

4,7-dichloro-3-(trifluoromethyl)quinoline

2-[(4-aminopentyl) (ethyl) amino] ethan-1-ol (66 mg, 0.38 mmol) and diisopropylethylamine (63 L, 0.38 mmol) are added to a suspension of 4,7-dichloro-3-(trifluoromethyl) quinoline (34 mg, 0.127 mmol) in 0.6 mL of N,N-dimethylformamide. The reaction medium is irradiated with microwaves for 20 min at 180° C. and then diluted in ethyl acetate and washed three times with a saturated NaCl solution. The organic phase is dried over MgSO$_4$, filtered and concentrated and then purified on a silica column with a 10/0 to 80/20 dichloromethane/methanol gradient.

Yield 19%. Colorless oil; HRMS calculated for $C_{19}H_{25}ClF_3N_3O$: 403.1638; Mass found: 403.1640

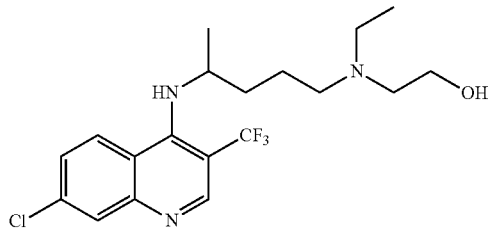 [SMILES: CCN(CCO)CCCC(C)Nc1c(C(F)(F)F)cnc2cc(Cl)ccc12]

4) A Compound of Formula (I) Where X═C(O)cPr

A solution of m-Chloroaniline (1.36 mL, 12.8 mmol), trimethyl orthoformate (15.37 mmol, 1.68 mL) and methyl 3-cyclopropyl-3-oxopropanoate (1.82 g, mmol) was heated at 130° C. for 5 hours in the presence of a Dean-Stark apparatus. The crude product is purified on a silica column with dichloromethane.

Yield 49%. White solid. RMN $^1$H (CDCl$_3$, 400 MHz) δ 0.90-0.94 (2H, m); 1.90-1.11 (2H, m); 3.19-3.25 (1H, m); 3.80 (1H, s); 7.01 (1H, dd, J=8.1, 2.3 Hz); 7.11-7.13 (1H, m); 7.16 (1H, t, J=2.3 Hz); 7.28 (1H, t, J=8.1 Hz); 8.40 (1H, d, J=12.9 Hz); 12.73 (1H, d, J=12.9 Hz). $^{13}$C (CDCl$_3$, 100 MHz) δ 11.9; 18.9; 51.6; 103.7; 116.1; 117.8; 125.5; 131.0; 135.9; 140.6; 151.0; 167.6; 202.1. SM (ESI$^+$): m/z=294 [M+1]

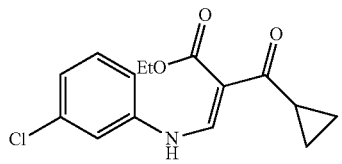

méthyl (Z/E)-3-((3-chlorophényl)amino)-2-(cyclopropanecarbonyl)acrylate
Methyl (Z/E-3-((3-chlorophenyl) amino-2 (cyclopropanecarbonyl)acrylate A suspension of methyl (Z/E-3-((3-chlorophenyl) amino-2 (cyclopropanecarbonyl)acrylate (500 mg, 1.7 mmol) in 5 mL of Dowtherm® is heated for 3 hours at 250° C. At ambient temperature, the medium is diluted in cyclohexane and filtered. The solid obtained is used without further purification.

Yield 31%. White solid; RMN $^1$H (DMSO, 400 MHz) δ 0.92-1.00 (4H, m); 3.55-3.62 (m, 1H); 7.46 (1H, dd, J=8.7, 2.0 Hz); 7.68 (1H, d, J=2.0 Hz); 8.23 (1H, d, J=8.7 Hz); 8.49 (1H, s); RMN $^{13}$C (DMSO, 100 MHz) δ 11.4; 19.0; 118.1; 125.1; 126.6; 128.0; 137.0; 139.8; 144.6; 174.7; 198.9. SM (ESI$^+$): m/z=248 [M+1]

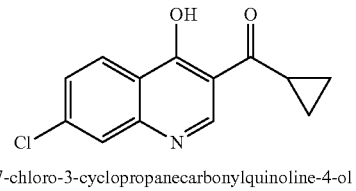

7-chloro-3-cyclopropanecarbonylquinoline-4-ol

A solution of 7-chloro-3-cyclopropanecarbonylquinoline-4-ol (50 mg, 0.218 mmol) and N,N-4-trimethylaniline (59 mg, 0.436 mmol) in 3 mL of toluene is heated at reflux under argon. The phosphoryl trichloride (37 mg, 0.239 mmol) is added and the reaction maintained at reflux for 16 hours. The reaction medium is extracted with dichloromethane and washed with a HCl 1N solution and then saturated with NaCl. The organic phase is dried over MgSO$_4$, filtered and concentrated. The product is purified by column of silica with dichloromethane.

Yield 90%. White solid. RMN $^1$H (DMSO, 400 MHz) δ 1.22-1.24 (4H, m); 2.73-2.67 (1H, m); 7.89 (1H, dd, J=8.9, 2.2 Hz); 8.24 (1H, d, J=2.2 Hz); 8.37 (1H, d, J=8.9 Hz); 9.00 (s, 1H); RMN $^{13}$C (DMSO, 100 MHz) δ 11.3; 19.0; 118.0; 125.0; 126.6; 128.0; 136.9; 139.8; 144.4; 174.7; 198.9. HRMS calculated for $C_{13}H_9Cl_2NO$: 265.0061; Mass found: 265.0063

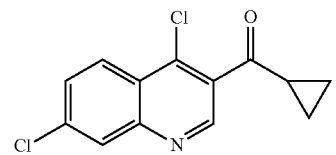

4,7-dichloro-3-cyclopropanecarbonylquinoline

To a suspension of 4,7-dichloro-3-cyclopropanecarbonylquinoline (48 mg, 0.180 mmol) in 1.2 mL of N,N-dimethylformamide is added 2-[(4-aminopentyl)(ethyl)amino]ethan-1-ol (94 mg, 0.540 mmol) and triethylamine (75 μL, 0.540 mmol). The reaction medium is irradiated with microwaves for 20 min at 180° C. and then diluted in ethyl acetate and washed three times with a saturated NaCl solution. The organic phase is dried over MgSO$_4$, filtered and concentrated and then purified on a silica column with a 10/0 to 80/20 dichloromethane/methanol gradient.

Yield 56%. Colorless oil; RMN $^1$H (CDCl$_3$, 400 MHz) δ 1.0 (3H, t, J=7.3 Hz); 1.03-1.07 (2H, m); 1.21-1.24 (2H, m); 1.42 (3H, d, J=6.5 Hz); 1.45-1.71 (4H, m); 2.48 (2H, t, J=7.2 Hz); 2.54-2.59 (4H, m); 2.65-2.71 (1H, m); 3.55 (2H, t, J=5.4 Hz); 4.19-4.26 (1H, m); 7.33 (1H, dd, J=9.1 Hz, J=2.1 Hz); 7.91 (1H, d, J=2.1 Hz); 8.04 (1H, d, J=9.1 Hz); 9.22 (1H, s); 10.60 (1H, d, J=8.7 Hz); RMN $^{13}$C (CDCl$_3$, 100 MHz) δ 11.35; 11.45; 17.76; 22.40; 23.58; 36.62; 47.54; 53.01; 53.51; 55.32; 58.36; 111.70; 118.05; 125.11; 127.76; 129.00; 137.53; 151.66; 153.33; 155.85; 201.44.

HRMS calculated for $C_{22}H_{30}ClN_3O_2$: 403.2026; Mass found: 403.2039

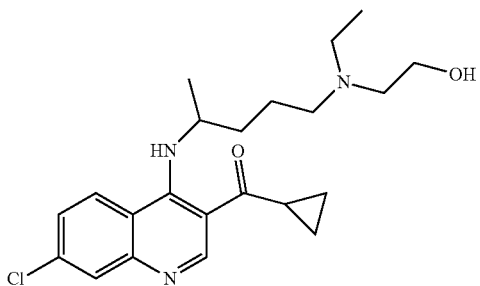 [SMILES: CCN(CCO)CCCC(C)Nc1c(C(=O)C2CC2)cnc2cc(Cl)ccc12]

5) A Compound of Formula (I) Where X=C(O)CF$_3$

A solution of 1-[7-chloro-4-(dimethylamino)quinolin-3-yl]-2,2,2-trifluoroethan-1-one (100 mg, 0.33 mmol) and 4-aminopentyl)(ethyl)amino]methanol (58.2 mg, 0.363 mmol) in 4 mL of acetonitrile is heated at 85° C. for 16 hours. The medium is concentrated and the residue is purified on a silica column with a 10/0 to 80/20 dichloromethane/methanol mixture.

Yield 21%. Colorless oil. RMN $^1$H (DMSO, 400 MHz) δ 0.89 (3H, t, J=6.9 Hz); 1.43 (3H, d, J=6.5 Hz); 1.39-1.51 (2H, m); 1.64-1.75 (2H, m); 2.42-2.54 (6H, m); 3.41 (2H, t, J=6.4 Hz); 4.41-4.44 (1H, m); 7.60 (1H, dd, J=9.1 Hz, 2.5 Hz); 7.91 (1H, d, J=2.5 Hz); 8.36 (1H, d, J=9.1 Hz); 8.73 (1H, q, J=2.3 Hz); 10.35 (1H, sl); RMN $^{13}$C (DMSO, 100 MHz) δ 11.1; 20.9; 28.9; 30.3; 35.1; 47.3; 52.6; 53.1; 55.1; 103.9; 116.6; 117.0; 125.9; 128.2; 128.9; 137.9; 150.7; 151.7; 156.9; 178.2.

HRMS calculated for C$_{20}$H$_{25}$ClF$_3$N$_3$O$_2$: 431.1587; Mass found: 431.1580

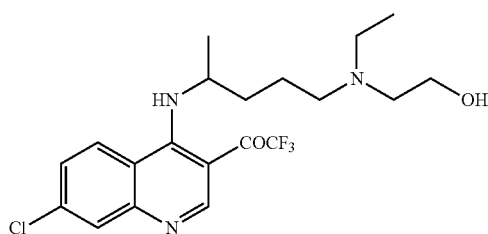

6) A Compound of Formula (I) Where X=Cl

To a suspension of 3,4,7-trichloroquinoline (50 mg, 0.21 mmol) in 0.5 mL of N-methyl-2-pyrrolidone are added (S)-2-[(4-aminopentyl)(ethyl)amino]ethan-1-ol (75 mg, 0.43 mmol), and triethylamine (60 µL, 0.43 mmol). The reaction medium is irradiated with microwaves for 45 min at 160° C. and then diluted in ethyl acetate and washed three times with a saturated NaCl solution. The organic phase is dried over MgSO$_4$, filtered, concentrated and then purified on a silica column with a 10/0 to 80/20 dichloromethane/methanol gradient.

Yield 94%. Colorless oil; RMN $^1$H (CDCl$_3$, 400 MHz) δ 1.07 (3H, t, J=7.2 Hz); 1.27 (3H, d, J=6.3 Hz); 1.56-1.73 (4H, m); 2.59-2.68 (6H, m); 3.61 (2H, t, J=4.5 Hz); 4.00-4.07 (1H, m); 4.47 (1H, d, J=9.8 Hz); 7.42 (1H, d, J=9.1 Hz, 2.3 Hz); 7.91 (1H, d, J=9.0 Hz); 7.96 (1H, d, J=2.1 Hz); 8.57 (1H, s). RMN $^{13}$C (CDCl$_3$, 100 MHz): 11.08; 22.49; 23.29; 36.38; 47.97; 51.08; 53.46; 54.40; 55.76; 58.10; 115.69; 120.59; 124.54; 126.71; 129.28; 135.32; 148.01; 148.96; 150.84. HRMS calculated for C$_{18}$H$_{25}$Cl$_2$N$_3$O: 369.13747; Mass found: 369.13797.

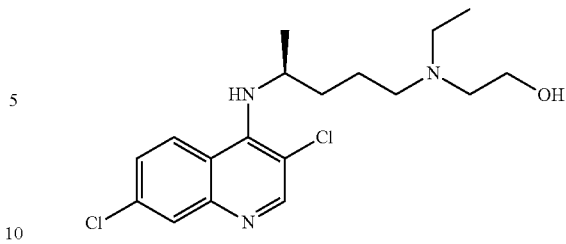

7) A Compound of Formula (I) Where X=Cl

To a suspension of 3,4,7-trichloroquinoline (50 mg, 0.21 mmol) in 0.5 mL of N-methyl-2-pyrrolidone are added (R)-2-[(4-aminopentyl)(ethyl)amino]ethan-1-ol (75 mg, 0.43 mmol), and triethylamine (60 µL, 0.43 mmol). The reaction medium is irradiated with microwaves for 45 min at 160° C. and then diluted in ethyl acetate and washed three times with a saturated NaCl solution. The organic phase is dried over MgSO$_4$, filtered, concentrated and then purified on a silica column with a 10/0 to 80/20 dichloromethane/methanol gradient.

Yield 85%. Colorless oil; RMN $^1$H (CDCl$_3$, 400 MHz) δ 1.08 (3H, t, J=7.3 Hz); 1.29 (3H, d, J=6.8 Hz); 1.59-1.73 (4H, m); 2.58-2.70 (6H, m); 3.62 (2H, t, J=4.9 Hz); 4.02-4.09 (1H, m); 4.49 (1H, d, J=10 Hz); 7.43 (1H, d, J=9.1 Hz, 2.2 Hz); 7.93 (1H, d, J=9.1 Hz); 7.98 (1H, d, J=2.2 Hz); 8.59 (1H, s). RMN $^{13}$C (CDCl$_3$, 100 MHz): 11.84; 20.12; 23.95; 34.25; 47.47; 48.87; 53.23; 55.21; 58.51; 100.42; 115.03; 127.44; 129.06; 129.26; 133.66; 150.42; 151.67; 151.98; HRMS calculated for C$_{18}$H$_{25}$Cl$_2$N$_3$O: 369.13747; Mass found: 369.13792.

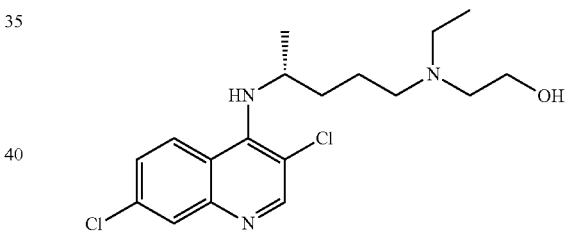

Thus, similarly to Examples 6) and 7), the preparation of compounds according to the present invention in the form of an enantiomerically pure mixture will be carried out by adding the aromatic chain (R) or (S)-2-[(4-aminopentyl)(ethyl)amino]ethan-1-ol in the last synthesis step.

8) A Compound of Formula (I) Where U and W=Cl

To a suspension of 4,5,7-trichloroquinoline (100 mg, 0.43 mmol) in 1 mL of N-methyl-2-pyrrolidone are added 2-[(4-aminopentyl)amino]ethan-1-ol (150 mg, 0.86 mmol), and triethylamine (120 µL, 0.86 mmol). The reaction medium is irradiated with microwaves for 45 min at 160° C. and then diluted in ethyl acetate and washed three times with a saturated NaCl solution. The organic phase is dried over MgSO$_4$, filtered, concentrated and then purified on a silica column with a 10/0 to 80/20 dichloromethane/methanol gradient.

Yield 60%. Colorless oil; 1H NMR (CDCl 3, 400 MHz) 1.04 (3H, t, J=7.2 Hz); 1.33 (3H, d, J=6.4 Hz); 1.57-1.73 (4H, m); 2.52-2.66 (6H, m); 3.56 (2H, t, J=5.3 Hz); 3.63-3.66 (1H, m); 6.38 (1H, d, J=5.6 Hz); 7.14 (1H, d, J=7.4 Hz); 7.33 (1H, d, J=2.2 Hz); 7.84 (1H, d, J=2.2 Hz); 8.43 (1H, d, J=5.6 Hz); 13C NMR (CDCl3, 100 MHz) 11.84; 20.12; 23.95; 34.25; 47.47; 48.87; 53.23; 55.21; 58.51; 100.42;

115.03; 127.44; 129.06; 129.26; 133.66; 150.42; 151.67; 151.98; HRMS calculated for C18H25Cl2N3O: 369.13747; Mass found: 369.13776.

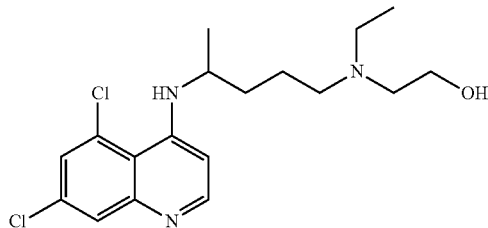 [SMILES: CCN(CCO)CCCC(C)Nc1ccnc2cc(Cl)cc(Cl)c12]

9) A Compound of Formula (I) Where U and W=Cl

To a suspension of 4,5,7-trichloroquinoline (79 mg, 0.34 mmol) in 0.5 mL of N-methyl-2-pyrrolidone are added (S)-2-[(4-aminopentyl)(ethyl)amino]ethan-1-ol (89 mg, 0.51 mmol), and triethylamine (95 µL, 0.68 mmol). The reaction medium is irradiated with microwaves for 45 min at 160° C. and then diluted in ethyl acetate and washed three times with a saturated NaCl solution. The organic phase is dried over MgSO₄, filtered, concentrated and then purified on a silica column with a 10/0 to 80/20 dichloromethane/methanol gradient.

Yield 60%. Colorless oil; RMN $^1$H (CDCl₃, 400 MHz) δ 1.05 (3H, t, J=7.2 Hz); 1.32 (3H, d, J=6.4 Hz); 1.59-1.71 (4H, m); 2.54-2.65 (6H, m); 3.58 (2H, t, J=5.3 Hz); 3.62-3.68 (1H, m); 6.37 (1H, d, J=5.6 Hz); 7.13 (1H, d, J=7.3 Hz); 7.31 (1H, d, J=2.2 Hz); 7.82 (1H, d, J=2.2 Hz); 8.41 (1H, d, J=5.6 Hz); RMN $^{13}$C (CDCl₃, 100 MHz) δ 11.84; 20.12; 23.95; 34.25; 47.47; 48.87; 53.23; 55.21; 58.51; 100.42; 115.03; 127.44; 129.06; 129.26; 133.66; 150.42; 151.67; 151.98; HRMS calculated for $C_{18}H_{25}Cl_2N_3O$: 369.13747; Mass found: 369.13652.

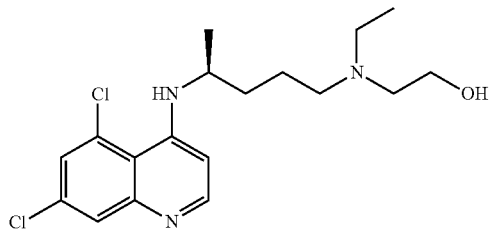 [SMILES: CCN(CCO)CCC[C@H](C)Nc1ccnc2cc(Cl)cc(Cl)c12]

10) A Compound of Formula (I) Where U and W=Cl

To a suspension of 4,5,7-trichloroquinoline (100 mg, 0.43 mmol) in 1 mL of N-methyl-2-pyrrolidone are added (R)-2-[(4-aminopentyl)(ethyl)amino]ethan-1-ol (150 mg, 0.86 mmol), and triethylamine (120 µL, 0.86 mmol). The reaction medium is irradiated with microwaves for 45 min at 160° C. and then diluted in ethyl acetate and washed three times with a saturated NaCl solution. The organic phase is dried over MgSO₄, filtered, concentrated and then purified on a silica column with a 10/0 to 80/20 dichloromethane/methanol gradient.

Yield 60%. Colorless oil; RMN $^1$H (CDCl₃, 400 MHz) δ 1.05 (3H, t, J=7.2 Hz); 1.32 (3H, d, J=6.4 Hz); 1.58-1.72 (4H, m); 2.53-2.67 (6H, m); 3.57 (2H, t, J=5.3 Hz); 3.62-3.67 (1H, m); 6.37 (1H, d, J=5.6 Hz); 7.13 (1H, d, J=7.3 Hz); 7.32 (1H, d, J=2.2 Hz); 7.83 (1H, d, J=2.2 Hz); 8.42 (1H, d, J=5.6 Hz); RMN $^{13}$C (CDCl₃, 100 MHz) δ 11.84; 20.12; 23.95; 34.25; 47.47; 48.87; 53.23; 55.21; 58.51; 100.42; 115.03; 127.44; 129.06; 129.26; 133.66; 150.42; 151.67; 151.98; HRMS calculated for $C_{18}H_{25}Cl_2N_3O$: 369.13747; Mass found: 369.1365.

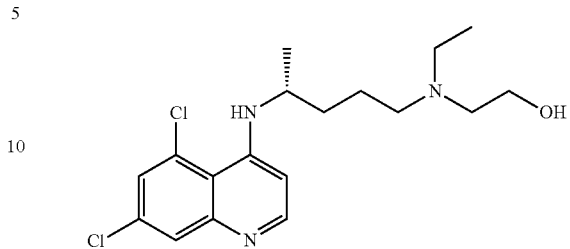

11) A Compound of Formula (I) Where U and V=Cl

To a suspension of 4,6,7-trichloroquinoline (100 mg, 0.43 mmol) in 1 mL of N-methyl-2-pyrrolidone are added 2-[(4-aminopentyl)(ethyl)amino]ethan-1-ol (150 mg, 0.86 mmol), and triethylamine (120 µL, 0.86 mmol). The reaction medium is irradiated with microwaves for 45 min at 160° C. and then diluted in ethyl acetate and washed three times with a saturated NaCl solution. The organic phase is dried over MgSO₄, filtered, concentrated and then purified on a silica column with a 10/0 to 80/20 dichloromethane/methanol gradient.

Yield 50%. Colorless oil; RMN $^1$H (CDCl₃, 400 MHz) δ 1.03 (3H, t, J=7.2 Hz); 1.32 (3H, d, J=6.4 Hz); 1.56-1.73 (4H, m); 2.47-2.62 (6H, m); 3.59 (2H, t, J=5.6 Hz); 3.66-3.72 (1H, m); 5.10 (1H, d, J=7.4 Hz); 6.40 (1H, d, J=5.6 Hz); 7.94 (1H, s); 8.04 (1H, s); 8.49 (1H, d, J=5.5 Hz). RMN $^{13}$C (CDCl₃, 100 MHz) δ 11.90; 20.51; 24.23; 34.45; 47.85; 48.67; 53.21; 55.01; 58.66; 99.71; 118.50; 121.49; 128.76; 131.03; 133.43; 147.92; 148.44; 152.33; HRMS calculated for $C_{18}H_{25}Cl_2N_3O$: 369.13747; Mass found: 369.13648.

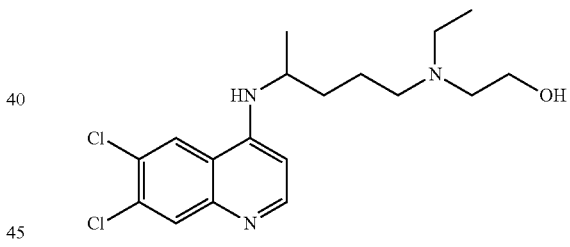

12) A Compound of Formula (I) Where U and Y=Cl

2-[(4-aminopentyl)(ethyl)amino]ethan-1-ol (150 mg, 0.86 mmol) and triethylamine (120 µL, 0.86 mmol) are added to a suspension of 4,7,8-trichloroquinoline (100 mg, 0.43 mmol) in 1 mL of N-methyl-2-pyrrolidone. The reaction medium is irradiated with microwaves for 45 min at 160° C. and then diluted in ethyl acetate and washed three times with a saturated NaCl solution. The organic phase is dried over MgSO4, filtered, concentrated and then purified on a silica column with a 10/0 to 80/20 dichloromethane/methanol gradient.

Yield 51%. Colorless oil; RMN $^1$H (CDCl₃, 400 MHz) δ 1.07 (3H, t, J=7.2 Hz); 1.30 (3H, d, J=6.4 Hz); 1.56-1.83 (4H, m); 2.58-2.69 (6H, m); 3.62 (2H, t, J=5.4 Hz); 3.65-3.73 (1H, m); 5.40 (1H, d, J=7.7 Hz); 6.43 (1H, d, J=5.5 Hz); 7.40 (1H, d, J=9.1 Hz); 7.80 (1H, d, J=9.1 Hz); 8.58 (1H, d, J=5.5 Hz); RMN $^{13}$C (CDCl₃, 100 MHz) δ 11.15; 20.46; 23.72; 34.23; 48.05; 48.75; 53.40; 55.31; 58.29; 99.91; 118.42; 119.56; 125.46; 131.76; 133.89; 146.38; 149.80; 152.22; HRMS calculated for $C_{18}H_{25}Cl_2N_3O$: 369.13747; Mass found: 369.13711.

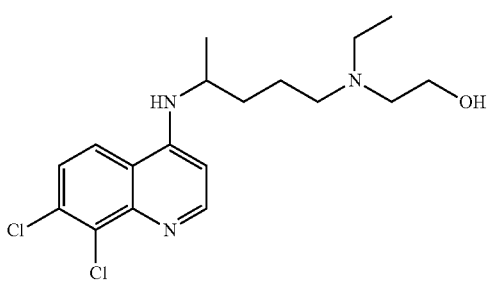 [SMILES: CCN(CCO)CCCC(C)Nc1ccnc2c(Cl)c(Cl)ccc12]

13) A Compound of Formula (I) Where X=Br

N-iodosuccinimide (626 mg, 2.78 mmol) is added to a suspension of 7-chloroquinolin-4-ol (500 mg, 2.78 mmol) in 16 mL of acetic acid. The reaction is heated at 60° C. for 5 hours and then diluted in water and filtered. The white solid is washed with water and dried under vacuum.

Yield 88%. White solid; RMN $^1$H (CDCl$_3$, 400 MHz) δ 7.41 (1H, d, J=8.7 Hz); 7.64 (1H, s); 8.13 (1H, d, J=8.8 Hz); 8.53 (1H, s); 12.32 (1H, sl); RMN $^{13}$C (CDCl$_3$, 100 MHz) δ 104.75; 117.68; 122.78; 124.33; 127.62; 136.45; 140.04; 140.77; 170.84; SM (ESI$^+$): m/z=257 [M+1].

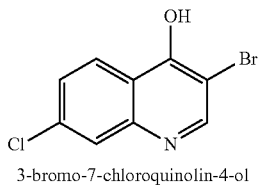 [SMILES: Oc1c(Br)cnc2cc(Cl)ccc12]

3-bromo-7-chloroquinolin-4-ol

A suspension of 7-chloro-3-bromoquinolin-4-ol (500 mg, 1.64 mmol) in 4.5 mL of phosphoryl trichloride is heated at 100° C. for 2 hours. Once at room temperature, the solution is poured into a water/ice mixture, filtered and washed with a saturated NaHCO$_3$ solution and then water. The resulting white solid is dried and used without further purification.

Yield 90%. White solid; RMN $^1$H (CDCl$_3$, 400 MHz) δ 7.86 (1H, dd, J=9.1, 2.1 Hz); 8.22 (1H, d, J=2.2 Hz); 8.27 (1H, d, J=6.1 Hz) 9.12 (1H, s); RMN $^{13}$C (CDCl$_3$, 100 MHz) δ 118.48; 126.08; 126.14; 129.12; 129.79; 136.74; 141.80; 147.75; 153.10; SM (ESI$^+$): m/z=275 [M+1].

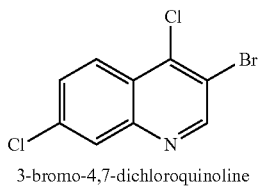 [SMILES: Clc1ccc2c(Cl)c(Br)cnc2c1]

3-bromo-4,7-dichloroquinoline

2-[(4-aminopentyl)(ethyl)amino]ethan-1-ol (188 mg, 1.08 mmol) and triethylamine (358 μL, 2.16 mmol) are added to a suspension of 3-bromo-4,7-trichloroquinoline (200 mg, 0.72 mmol) in 2 mL of N-methyl-2-pyrrolidone. The reaction medium is irradiated with microwaves for 45 min at 160° C. and then diluted in ethyl acetate and washed three times with a saturated NaCl solution. The organic phase is dried over MgSO$_4$, filtered, concentrated and then purified on a silica column with a 10/0 to 80/20 dichloromethane/methanol gradient.

Yield 11%. Colorless oil; RMN $^1$H (CDCl$_3$, 400 MHz) δ 1.04 (3H, t, J=7.2 Hz); 1.28 (3H, d, J=6.4 Hz); 1.55-1.66 (4H, m), 2.51-2.54 (2H, m); 2.59-2.64 (4H, m); 3.58 (t, J=5.3 Hz, 2H); 3.96-4.04 (1H, m); 4.46 (1H, d, J=10.3 Hz); 7.41 (1H, dd, J=9.1, 2.3 Hz); 7.92 (1H, d, J=9.1 Hz); 7.97 (1H, d, J=2.2 Hz); 8.69 (1H, s); RMN $^{13}$C (CDCl$_3$, 100 MHz) δ 11.42; 22.37; 23.59; 36.57; 47.68; 53.29; 55.04; 55.35; 58.28; 107.35; 120.89; 124.89; 126.50; 129.13; 135.36; 149.42; 149.65; 152.69; HRMS calculated for C$_{18}$H$_{25}$BrClN$_3$O: 413.0869; Mass found: 413.0867.

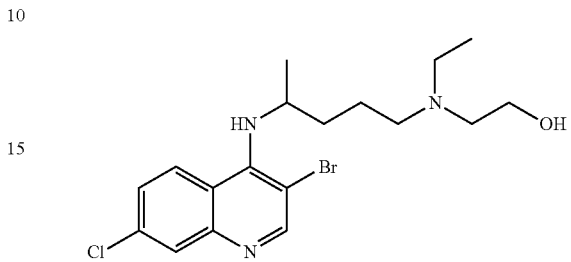

14) A Compound of Formula (I) Where X=cPr 4,7-Dichloro-3-iodoquinoline (350 mg, 1.08 mmol) and cyclopropylboronic acid (139 mg, 1.63 mmol) are dissolved in a degassed solution of 0.5 M aqueous THF/K$_3$PO$_4$ (1/2; 4 mL/8 mL). The XPhos Pd G2 catalyst (42 mg, 0.054 mmol) is added under argon and the reaction is heated at 80° C. for 2 hours. At room temperature, the reaction medium is filtered through Celite® and then extracted twice with dichloromethane. The organic phase is washed with water and dried over MgSO$_4$, filtered, concentrated and then purified on a silica column with a 5/5 to 2.5/7.5 cyclohexane/dichloromethane gradient.

Yield 26%. Colorless oil; RMN $^1$H (CDCl$_3$, 400 MHz) δ 0.89-0.93 (2H, m); 1.16-1.21 (2H, m); 2.29-2.36 (1H, m); 7.56 (dd, J=9.03, 1.76 Hz, 1H); 8.05 (1H, d, J=2.01 Hz, 1H), 4.62 (1H, m); 7.71 (1H, dd, J=9.1, 2.3 Hz); 7.9 (1H, d, J=2.2 Hz); 8.18 (1H, d, J=8.1 Hz); 8.59 (1H, d, J=9.1 Hz); 8.69 (1H, s); 9.14 (1H, sl); RMN $^{13}$C (CDCl$_3$, 100 MHz) δ 7.88; 12.07; 124.68; 125.31; 128.43; 128.52; 133.42; 135.15; 142.06; 147.59; 149.85; SM (ESI$^+$): m/z=238 [M+1].

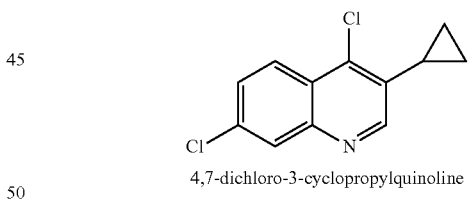

4,7-dichloro-3-cyclopropylquinoline

2-[(4-aminopentyl)(ethyl)amino]ethan-1-ol (75 mg, 0.43 mmol) and diisopropylethylamine (143 μL, 0.87 mmol) are added to a suspension of 4,7-dichloro-3-cyclopropylquinoline (69 mg, 0.29 mmol) in 0.5 mL of N-methyl-2-pyrrolidone. The reaction medium is irradiated with microwaves for 45 min at 160° C. and then diluted in ethyl acetate and washed three times with a saturated NaCl solution. The organic phase is dried over MgSO$_4$, filtered, concentrated and then purified on a silica column with a 10/0 to 80/20 dichloromethane/methanol gradient.

Yield 21%. Colorless oil; RMN $^1$H (CDCl$_3$, 400 MHz) δ 0.68-0.77 (2H, m); 1.07 (2H, m); 1.17 (3H, t, J=7.3 Hz); 1.26 (1H, m); 1.27 (3H, d, J=6.27); 1.60-1.82 (8H, m); 2.72 (2H, m); 2.79-2.82 (4H, m); 3.72 (2H, m); 4.12 (1H, sl); 4.61 (1H, sl); 7.39 (1H, dd, J=9.1, 2.0 Hz, 1H); 7.94 (1H, d, J=9.1 Hz); 7.99 (1H, d, J=2.0 Hz); 8.50 (1H, s); RMN $^{13}$C (CDCl$_3$, 100

MHz) δ 6.01; 6.06; 22.29; 30.94; 36.14; 48.17; 53.52; 53.64; 55.93; 57.57; 119.03; 120.47; 124.39; 125.65; 128.19; 134.62; 151.83; 152.12; HRMS mass calculated for $C_{21}H_{30}ClN_3O$ 375.20774; Mass found: 375.20701.

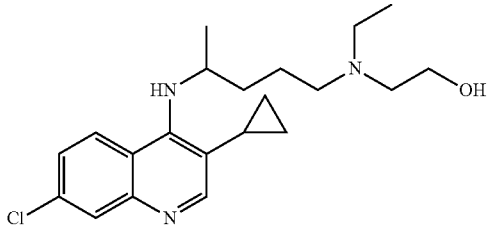 [SMILES: CCN(CCO)CCCC(C)Nc1c(C2CC2)cnc2cc(Cl)ccc12]

15) A Compound of Formula (I) Where $X=CH_2OCH_2C≡CH$

A solution of ethyl-4,7-dichloroquinoline-3-carboxylate (270 mg, 1 mmol) is added, at 0° C., in 5 mL of anhydrous THF to a suspension of $LiAlH_4$ (56 mg, 1.49 mmol) in 30 mL of anhydrous THF. After stirring for 3 hours at room temperature, the reaction is neutralized with 1N aqueous sodium hydroxide solution and extracted 5 times with ethyl acetate. The organic phase is washed with a silica column with a 10/0 to 95/5 dichloromethane/methanol gradient.

Yield 50%. White solid; RMN $^1H$ ($CDCl_3$, 400 MHz) δ 5.05 (1H, d, J=5.7 Hz); 7.62 (1H, dd, J=9.0 Hz, 2.2 Hz); 8.14 (1H, d, J=2.0 Hz); 8.21 (1H, d, J=9.0 Hz); 9.02 (1H, s); RMN $^{13}C$ ($CDCl_3$, 100 MHz) δ 58.98; 123.91; 125.65; 127.94; 128.71; 132.68; 134.74; 138.55; 147.82; 151.53; SM ($ESI^+$): m/z=228 [M+1].

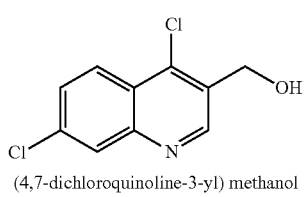 [SMILES: OCc1cnc2cc(Cl)ccc2c1Cl]

(4,7-dichloroquinoline-3-yl) methanol

NaH (46 mg, 1.93 mol) is added, in small portions, to a solution of 4,7-dichloroquinolin-3-yl) methanol (110 mg, 0.48 mmol) in 8 mL of anhydrous THF at 0° C.; after stirring for 10 min, 3-bromopropyne (430 mg, 2.9 mmol) is added drop by drop. After one night at ambient temperature, the medium is neutralized with ice, diluted with ethyl acetate and washed 4 times with saturated NaCl solution. The organic phase is dried over $MgSO_4$, filtered and concentrated in vacuum. The residue is purified on a silica column with a 10/0 to 90/10 dichloromethane/methanol gradient.

Yield 62%. RMN $^1H$ ($CDCl_3$, 400 MHz) δ 2.54 (1H, t, J=2.3 Hz); 4.33 (2H, d, J=2.3 Hz); 4.92 (1H, s); 7.6 (1H, dd, J=8.9 Hz, 2.1 Hz); 8.12 (1H, d, J=2.3 Hz); 8.19 (1H, d, J=8.8 Hz); 8.95 (1H, s).

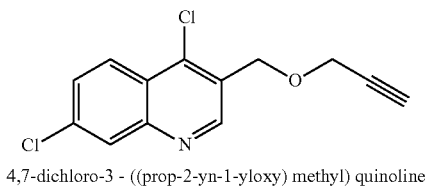 [SMILES: C#CCOCc1cnc2cc(Cl)ccc2c1Cl]

4,7-dichloro-3 - ((prop-2-yn-1-yloxy) methyl) quinoline

2-[(4-aminopentyl)(ethyl) amino]ethan-1-ol (104 mg, 0.60 mmol) and triethylamine (83 μL, 0.60 mmol) are added to a suspension of 4,7-dichloro-3-((prop-2-yn-1-yloxy) methyl) quinoline (80 mg, 0.30 mmol) in 1 mL of N-methyl-2-pyrrolidone. The reaction medium is irradiated with microwaves for 45 min at 160° C. and then diluted in ethyl acetate and washed three times with a saturated NaCl solution. The organic phase is dried over $MgSO_4$, filtered, concentrated and then purified on a silica column with a 10/0 to 80/20 dichloromethane/methanol gradient.

Yield 31%. Yellow oil; RMN $^1H$ ($CDCl_3$, 400 MHz) δ 1.08 (3H, t, J=7.1 Hz); 1.25-1.28 (4H, m); 1.59-1.74 (4H, m); 2.63-2.57 (3H, m); 2.66-2.72 (4H, m); 3.63 (2H, t, J=4.9 Hz); 3.98-4.05 (1H, m); 4.21 (2H, d, J=2.3 Hz); 4.73 (2H, s); 4.92 (1H, d, J=9.7 Hz); 7.38 (1H, dd, J=9.4, 2.3 Hz); 7.95-7.98 (2H, m); 8.48 (1H, s); RMN $^{13}C$ ($CDCl_3$, 100 MHz) δ 11.06; 22.59; 23.40; 36.53; 47.90; 53.39; 54.14; 55.53; 57.24; 58.01; 68.27; 75.92; 79.32; 114.89; 119.90; 125.18; 125.76; 128.86; 135.44; 150.76; 152.80; 152.95; HRMS mass calculated for $C_{22}H_{30}ClN_3O_2$: 403.20265; Mass found: 403.20029.

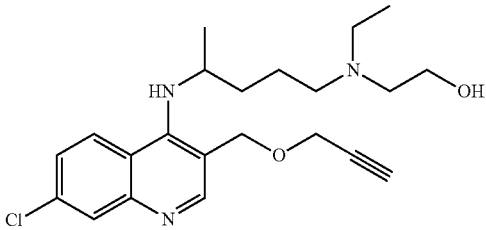 [SMILES: C#CCOCc1cnc2cc(Cl)ccc2c1NC(C)CCCN(CC)CCO]

Affinity of Compounds with MPO and αB-C

Using the surface plasmon resonance technology (Biacore 3000), the interaction constants between HCQ analogues (HCQa) and myeloperoxidase (MPO) targets and αB-crystalline (αB-C) were measured at 25° C. according to 12 different series of experiments. First, HCQ analogues at five different concentrations ($10^{-6}$ to $10^{-8}$ M) were injected at a rate of $10^{-6}$ L/min for 250 s on the MPO and αB-C targets as well as on the ERK1 and ERK2 controls, followed by a dissociation phase of 150 s.

The kinetic parameters were measured using the BIAevaluation 4.1 software. The set of resonance unit values obtained with the controls were subtracted from those obtained with MPO and αB-C to compensate for non-specific bonds. The results of these affinity tests are shown in Tables 1 and 2.

The differences in Kd values for the myeloperoxidase (MPO) and αB-crystalline (αB-C) enzymes in Tables 1 and 2 are due to the variability of commercial batches. Nevertheless, the difference between the Kd of the compounds HCQ and CB137 remains identical according to these two tests.

TABLE 1

| Molecules | Reference | $K_d$ (M) on MPO | $K_d$ (M) on crystallin |
|---|---|---|---|
| 7-chloro-quinoline with HN-CH(CH₃)-(CH₂)₃-N(Et)-CH₂CH₂OH side chain; H₂SO₄ | Commercial HCQ | $7.1e^{-7}$ | $2.2e^{-8}$ |
| 7-chloro-3-chloro-quinoline with HN-CH(CH₃)-(CH₂)₃-N(Et)-CH₂CH₂OH side chain; H₂SO₄ | CB137 | $6.59e^{-9}$ | $1.75e^{-7}$ |
| 7-chloro-quinoline with HN-CH(CH₃)-(CH₂)₃-N(Et)-CH₂CH₂OH side chain; TFA | CB133 | $7.11e^{-7}$ | $2.19e^{-9}$ |
| 7-chloro-3-chloro-quinoline with HN-CH(CH₃)-(CH₂)₃-N(Et)-CH₂CH₂OH side chain; TFA | CB072 | $1.1e^{-9}$ | $1.6e^{-7}$ |
| 7-chloro-3-cyano-quinoline with HN-CH(CH₃)-(CH₂)₃-N(Et)-CH₂CH₂OH side chain; TFA | CB029 | $7.1e^{-8}$ | $3.5e^{-8}$ |
| 7-chloro-3-trifluoromethyl-quinoline with HN-CH(CH₃)-(CH₂)₃-N(Et)-CH₂CH₂OH side chain; TFA | CB108 | $1.4e^{-8}$ | $8.1e^{-7}$ |

TABLE 1-continued

| Molecules | Reference | $K_d$ (M) on MPO | $K_d$ (M) on crystallin |
|---|---|---|---|
| 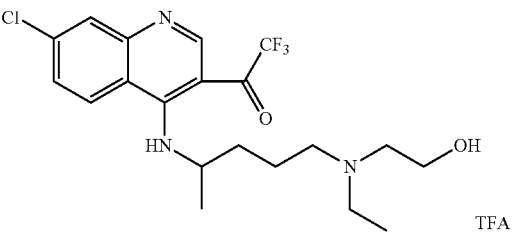 TFA | CB114 | $6.0e^{-8}$ | $2.2e^{-5}$ |
| 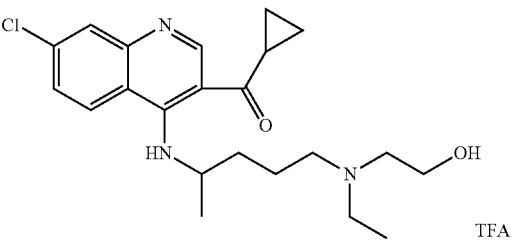 TFA | CB103 | $3.6e^{-8}$ | $6.6e^{-7}$ |
| 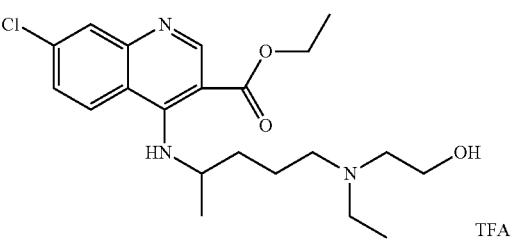 TFA | NT36F9 | $7.5e^{-9}$ | Kd not measurable because below the detection threshold |
| 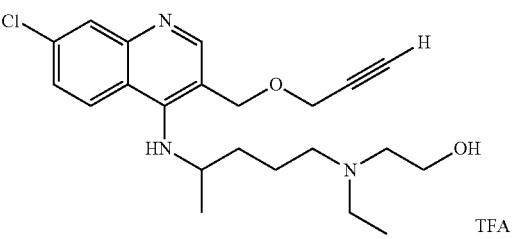 TFA | NT69 | $7.1e^{-9}$ | Kd not measurable because below the detection threshold |

Analysis of the compounds in the form of sulphate salts according to the method described above:

TABLE 2

| Molecules | Reference | $K_d$ (M) on MPO | $K_d$ (M) on crystallin |
|---|---|---|---|
| 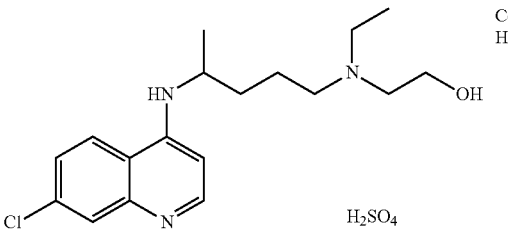 H$_2$SO$_4$ | Commercial HCQ | $4 \times 10^{-6}$ | $1 \times 10^{-6}$ |

TABLE 2-continued
| Molecules | Reference | $K_d$ (M) on MPO | $K_d$ (M) on crystallin |
|---|---|---|---|
| 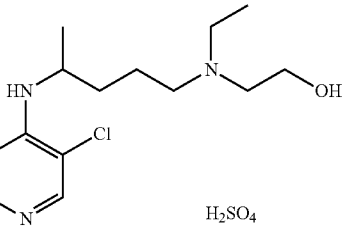 H₂SO₄ | CB137 | $6 \times 10^{-8}$ | $3 \times 10^{-5}$ |
| 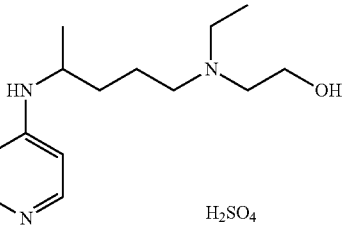 H₂SO₄ | CB300 | $4 \times 10^{-6}$ | $2 \times 10^{-4}$ |
| 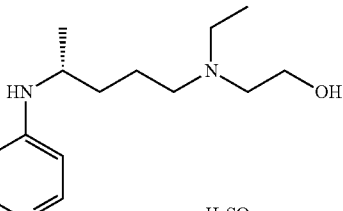 H₂SO₄ | CB321 R-enantiomer | $7 \times 10^{-6}$ | $1 \times 10^{-5}$ |
| 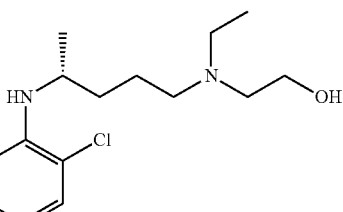 H₂SO₄ | CB323 R-enantioer | $9 \times 10^{-8}$ | $2 \times 10^{-4}$ |
| 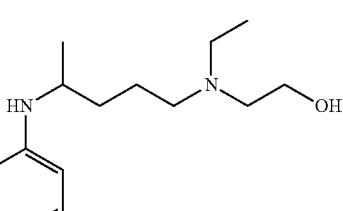 H₂SO₄ | CB317 | $9 \times 10^{-6}$ | $1 \times 10^{-4}$ |
| 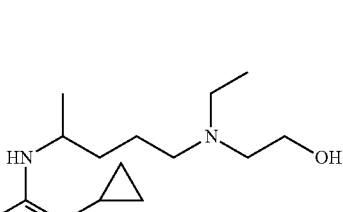 H₂SO₄ | CB341 | $5 \times 10^{-6}$ | $2 \times 10^{-5}$ |

Efficacy of CB137 in a Lupus Model

Animals

The MRL/MPJ-Fas (lpr) (MRL-lpr) and C57Bl/6 mice for the behavioral experiments are from the Jackson Laboratory and are randomly distributed into 5 groups. All animals were kept at controlled temperature (23° C.+/−1° C.) with a 12-hour day/night cycle, water and ad libitum food.

Treatment with HCQ or CB137

Mice received the specified dose of hydroxychloroquine (Tokyo Chemical Industry), CB137 or carrier intraperitoneally (IP), every 24 hours and for 5 days over a 10-week period. With regard to the MRL/lpr mice, treatment started at 7 weeks of age, and ended at 23 weeks of age where a significant proportion of untreated mice died. With regard to the C57B1/6 mice, the same treatment program was carried out and the mice were sacrificed after 70 IP injections. HCQ and CB137 were each freshly prepared in physiological saline and injected into the mice in a final volume of 50 µL. The MRL/lpr mice were examined daily for skin lesions. For histological analysis, the animals were sacrificed and the tissues were rapidly dissected and immediately post-fixed.

All animal experiments were carried out under the supervision of authorized investigators and according to the current EU regulations. The experiments were approved by the Local and National Ethics Committee under registration number 02.952,01.

Survival of MRL/lpr Mice (Lupus Model)

The mice that are injected via the IP route with CB137 at 10 mg/kg have a significantly higher survival rate than the HCQ mice treated with the same dose (FIG. 1).

Development of the Disease

Figure 2:
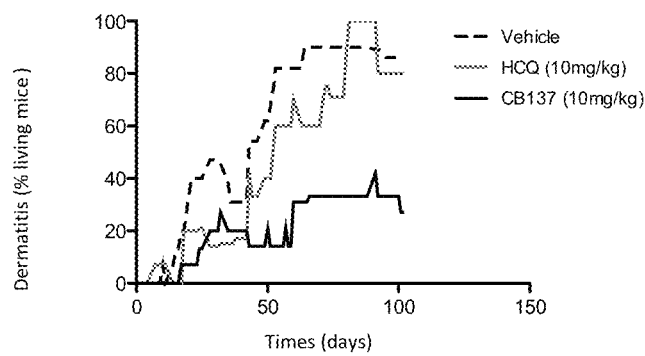
FIG. 2 shows the rate of mice having dermatitis treated with HCQ (10 mg/kg) or CB137 (10 mg/kg)

Dermatitis was less common in mice treated with CB137 10 mg/kg compared to control (carrier) mice and HCQ treated mice (10 mg/kg (FIG. 2).

Determination of Retinopathy

In order to demonstrate that the accumulation of HCQ in the back (retina) may lead to retinopathy, the following tests were performed.

Test of the visual cliff: Mice are placed on a sheet of horizontal glass under which there is, on one side, a surface with regular texture (a grid) glued directly under the glass, and, on the other side, the same textured surface but much lower beneath the glass. The score is based and calculated on the percentage of steps taken on the high part and on the part above the void.

Visual placement test: Mice are raised by the tail about 15 cm above the ground and then lowered in decelerated manner towards the ground. The score is based on the distance between the nose of the mouse and the grid before the animal stretches its anterior limbs in the direction of the grid.

Histology: 7-week-old mice are injected with 10 mg/kg HCQ or 5, 10 and 15 mg/kg of the CB137 analog 5 times weekly for a period of 62 days. After assigning them a number, the mice are randomized according to their weight and treatment. The mice are divided in groups of 5 in cages, one mouse being treated with the carrier, one with HCQ 10 mg/kg, one with CB137 5 mg/kg, one with CB137 10 mg/kg and one with CB137 15 mg/Kg. The mice are housed in an environment maintained at a temperature of 22° C., 35-55% humidity and with 12-hour cycles of light/darkness.

At the end of the experiment, the mice are euthanized by cervical dislocation. The eyeballs are isolated and stored in a solution containing 4% paraformaldehyde, 5% glutaraldehyde and 0.1 M sodium cacodylate overnight at 4° C. The samples are washed, dehydrated and embedded in paraffin. The 4-µm retinal sections are stained with 1% toluidine blue followed by 1% methylene blue. The retinal toxicity of the samples is then determined by analysis of the sections under microscope.

Figure 3:
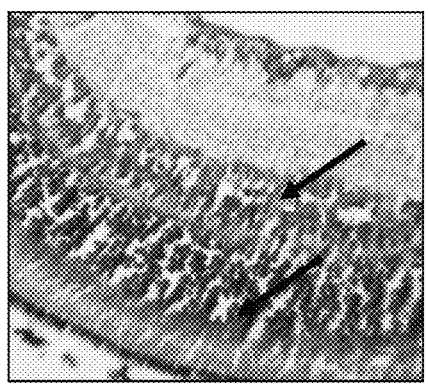
FIG. 3 shows two representative photographs of a cross-section of the retina.
Figure 3:
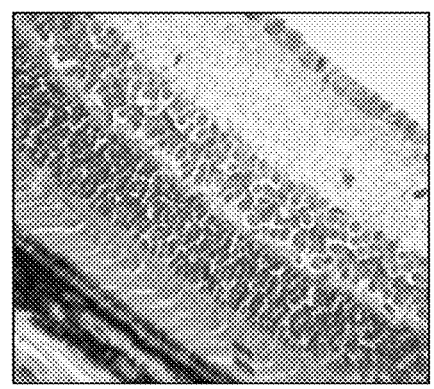
Figure 4:
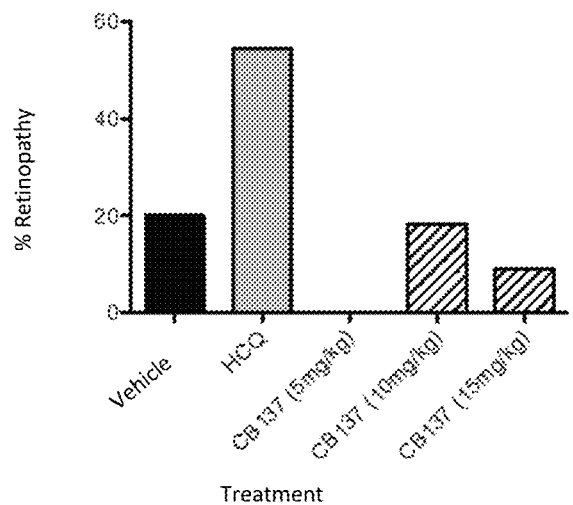
FIG. 4 shows the percentage of treated mice showing retinal lesions according to the treatment.

Histological analysis of the retina of mice treated with HCQ, CB137 shows that HCQ induces retinal lesions. CB137, meanwhile, does not induce more lesions than in the control mice (carrier) (FIGS. 3 and 4). FIG. 3 shows two representative photographs of a retinal cross-section (with toluidine and methylene blue staining) with the left photo showing the retina of a mouse treated with 10 mg/kg HCQ (retinal damage indicated by the arrows), and the right photo showing the healthy retina of a mouse treated with 10 mg/kg CB137.

Efficacy of CB137 in a Vasculitis Model

Mouse

Female C57Bl/6 strain mice from the Jackson Laboratory, 8-10 weeks old and weighing about 20 g, are used in all experiments. The mice are maintained at a temperature of 23° C.±1° C. with 12-hour light/dark cycle. Mice have access to water and food ad libitum and are housed at least one week before the beginning of any experiments.

Preparation of Bovine Serum Albumin (BSA) Antibody

The gamma-globulin fraction of a hyperimmune serum from a rabbit immunized with bovine serum albumin (BSA) was obtained by precipitation with ammonium sulphate and the fraction obtained was then dialyzed. The concentration of immunoglobulins was assessed by a protein assay using the bicinchoninic acid (BCA) method (ThermoFisher, Strasbourg, France). The enrichment of the anti-BSA antibody was verified by direct ELISA.

Model of Pulmonary Vasculitis Induced by Immune Complexes

A retro-orbital blood sampling was performed using capillaries containing heparin on mice anesthetized with isoflurane the day before the manipulation. The next day, the mice were anesthetized with a mixture of ketamine and xylasin (90 mg/kg and 125 mg/kg, respectively). The immune IgG complex is induced in the lungs by intratracheal instillation of 0.5 mg of anti-BSA rabbit antibody (MP Biomedicals, Strasbourg, France) and by the administration of 0.5 mg per mouse of BSA antigen in the caudal vein (Warner et al., 2001 and Warren et al., 1989). The specified treatment (PF-1355, CB137 or solvent alone) is administered enterally. The animals are euthanized 4 hours after intratracheal instillation.

Removal of Bronchoalveolar Fluid and Quantification of Cells

The animals are euthanized 4 hours after the intratracheal instillation by a lethal injection of pentobarbital. A submandibular blood sample is taken. The thoracic cage is open so as to reveal the lungs and the trachea. To recover the bronchoalveolar fluid, a probe is placed in the trachea and the lungs are washed three times with 0.5 mL of saline supplemented with 2.5 mM EDTA at pH 7.4. The cells are centrifuged after each wash. The supernatant of the first lavage is preserved to measure the activity of the MPO and the supernatants resulting from the subsequent washings are eliminated. The cell pellets, for each mouse, are pooled and resuspended in 200 µL of PBS. Red blood cells are removed with hypotonic solution (Lonza, Basel, Switzerland). The total number of cells, excluding any residual red cells and dead cells stained with trypan blue, is determined under the light microscope on a Malassez cell.

Flow Cytometry

The cells resulting from the bronchoalveolar lavages are placed in PBS supplemented with 2.5 mM EDTA and 2% fetal calf serum and labeled at 4° C. for 20 minutes using monoclonal antibodies directly coupled to a fluorochrome: APC Rat Anti-mouse F4/80 (clone BM8, final concentration 2 µg/mL, eBiosciences, Switzerland); PE Rat Anti-Mouse Gr-1 (clone RB6-8C5, final concentration 2 µg/mL, BD, USA) and FITC Rat Anti-Mouse CD45 (clone 30F11; final concentration 5 µg/mL; BD, USA). The cells are then centrifuged (two minutes at 300 g), then resuspended in PBS supplemented with 2.5 mM EDTA and 2% fetal calf serum, and the cell death marker 7-AAD (final concentration 1.25 µg/mL; BD, USA) is added to identify dead cells. The experimental data are acquired using FACSCalibur (BD, USA). Analysis by FlowJo software (Treestar, OR, USA) allows excluding dead cells (7-AAD++) and quantifying the proportions of pneumocytes (CD45−), macrophages (CD45++ F4/80+ Gr-1+) and neutrophils (CD45+ F4/80− Gr-1++) in the bronchoalveolar lavage.

Figure 5:
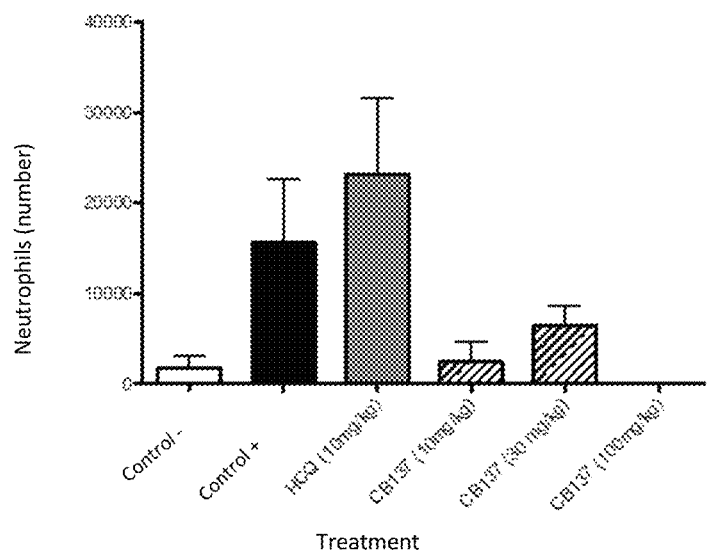
FIG. 5 shows the number of neutrophils presentin the lungs of mice treated with HCQ (10 mg/kg or CB 137 (10, 30 and 100 mg/kg).

Induction of the vasculitis model results in an increase in neutrophils present in the bronchoalveolar lavages. HCQ appears to slightly increase the amount of neutrophils compared to control +. In contrast, CB137 decreases the amount of neutrophils present in the lungs (FIG. 5).

Preparation of Lung Sections

The lungs are retrieved and then fixed in 4% PFA (1 hour at room temperature and then overnight at 4° C.). They are then washed in two 1×PBS baths for 10 minutes. They are dehydrated in a series of ethanol baths (2 baths of 15 minutes) of increasing concentration (25%, 50%, 75%, 95% and 100%). Once dehydrated, the lungs are immersed in two baths of toluene for 4 hours and then embedded in paraffin. The paraffin blocks are then cut into 4-µm-thick sections. Lung sections are stained with hematoxylin and eosin. The slides are immersed in 2 baths of toluene for 5 minutes and then in alcohol baths of decreasing concentrations (100%, 95%, 75%, 50% and 25%) for 5 minutes each, then in 2 baths of water for 5 minutes. The slides are then immersed in a solution of hematoxylin for 2.5 minutes and rinsed under running water for 15 minutes. They are then immersed in an eosin bath for 5 minutes, rinsed in 2 baths of 100% ethanol for 30 seconds and then immersed in 2 baths of toluene for 10 minutes.

Various sections are recovered to be stained using the Masson trichrome staining kit from Roth (#7089). The first part of the protocol is the same (toluene, ethanol and then water). The slides are then immersed in a hematoxylin bath of the kit (solution A+B ratio 1:1) for 2.5 minutes and then rinsed under running water for 15 minutes. The slides are plunged successively into Goldner no. 1 staining (5 minutes) followed by 1% acetic acid (30 seconds), Goldner no. 2 staining (2 minutes), in 1% acetic acid (30 seconds), Goldner no. 3 staining (3 minutes), in 1% acetic acid (2 minutes), in two 100% ethanol baths (2×3 seconds) and in 2 toluene baths (2×10 minutes).

Histological Analysis of Lung Sections

The lung sections are examined under a light microscope (Axio LabA1 by Zeiss brand) to assess the intensity of the neutrophil influx and the level of hemorrhage, and to identify the structural alterations. A minimum of 10 fields at 400× magnification is analyzed per animal.

Figure 6:
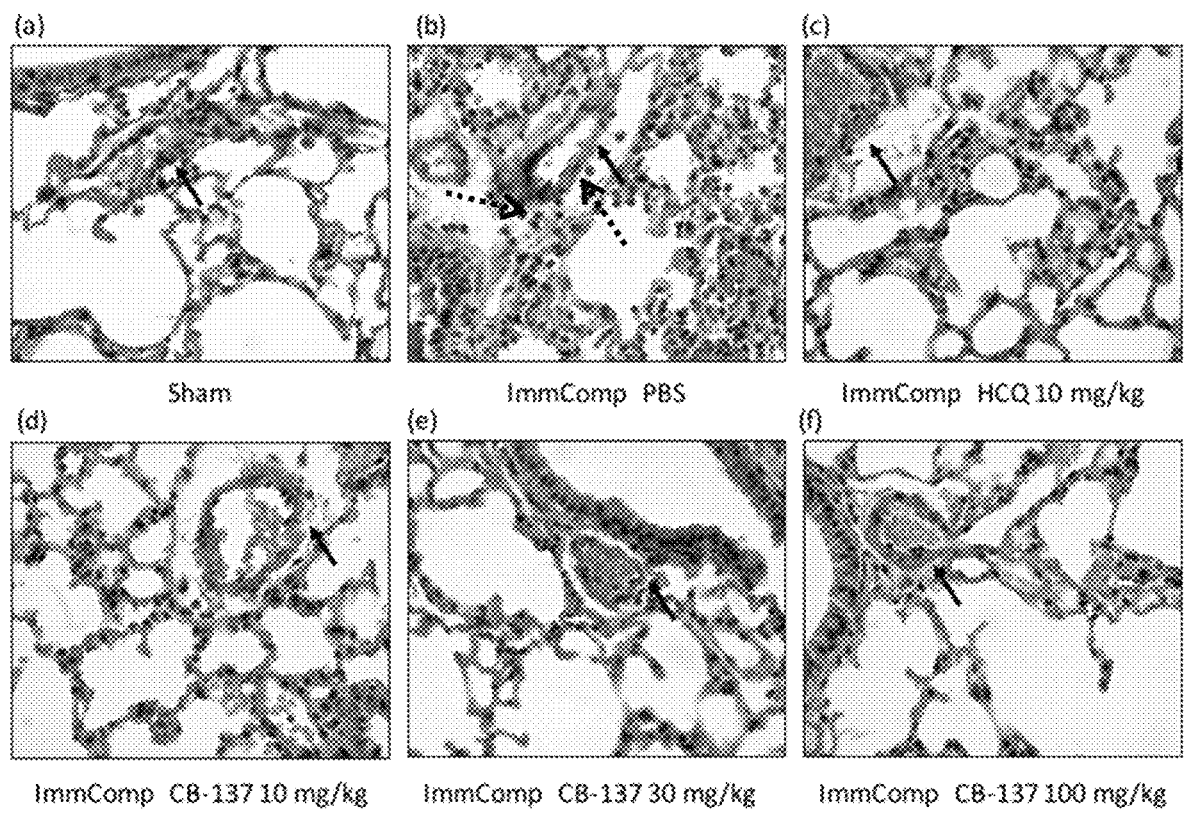
FIG. 6 shows lung sections stained with eosin and hematoxylin.

CB137 and HCQ allow inhibiting pulmonary vasculitis induced by immune complexes. The mice were treated with PBS, HCQ (10 mg/kg) or CB137 (10, 30 or 100 mg/kg) per os prior to the induction of pulmonary vasculitis. Briefly, these vasculitides are induced by instilling an anti-BSA antibody (50 µg) into the lungs and the respective antigen into the vein of the tail. The photos (FIG. 6) represent sections of lungs stained with eosin and hematoxylin. (a) negative control (b) Induction of immune complexes (ImmComp) with solvent (c) with 10 mg/kg HCQ (d) with 10 mg/kg CB137 (e) with 30 mg/kg CB137 (f) with 100 mg/kg CB137. In FIG. 6, the solid line arrows indicate the blood vessels. Also noteworthy is the large influx of neutrophils (identified by dotted arrows) and the hemorrhage in (b).

These results indicate that the CB137 compound limits pulmonary inflammation induced by immune complexes.

The invention claimed is:

1. A compound of formula (I), its pharmaceutically acceptable salt, solvate, or hydrate, in the form of an enantiomer or a mixture of enantiomers:

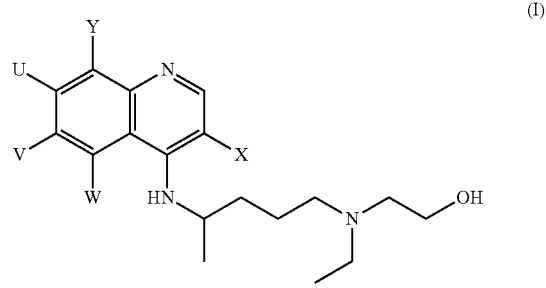

(I)

In which U represents:
F, Cl, Br, CN, or $N_3$;
and V, W and Y independently represent:
H;
Cl, Br, CN, or $N_3$;
and X represents:
H, provided that V, W, X and Y do not all simultaneously represent H;
Cl, Br, CN, or $N_3$;
$Si(R^a)(R^b)(R^c)$, where
$R^a$, $R^b$, and $R^c$, which may be identical or different, represent a $C_1$ to $C_6$, alkyl group or unsubstituted aryl group;
$R^1$, where
$R^1$ represents a $C_1$ to $C_6$ alkyl group; a $C_1$ to $C_6$ perfluoroalkyl group;
cycloalkyl; unsubstituted aryl; unsubstituted aralkyl; or unsubstituted heteroaryl;
$S(O)_n R^2$, where
n=0, 1, or 2,
$R^2$ represents a $C_1$ to $C_6$ alkyl group; unsubstituted aryl; unsubstituted aralkyl; or unsubstituted heteroaryl,
$NR^3R^4$, where
$R^3$ represents H, a $C_1$ to $C_6$ alkyl group; cycloalkyl; unsubstituted aryl; unsubstituted aralkyl; or unsubstituted heteroaryl,
$R^4$ represents H; a $C_1$ to $C_6$ alkyl group; cycloalkyl; unsubstituted aryl; unsubstituted aralkyl; unsubstituted heteroaryl; C(O)—$C_1$ to $C_6$ alkyl; C(O)-cycloalkyl; C(O)-unsubstituted aryl; C(O)-unsubstituted aralkyl; C(O)-unsubstituted heteroaryl; $SO_2$—$C_1$ to $C_6$-alkyl; $SO_2$-cycloalkyl; $SO_2$-unsubstituted aryl; $SO_2$-unsubstituted heteroaryl; $C(O)N(R^5)_2$; where $R^5$ is as defined for $R^3$; $C(O)OR^6$, where $R^6$ represents a $C_1$ to $C_6$ alkyl group; or unsubstituted aralkyl; or $R^3$ and $R^4$ may be joined together to form a non-aromatic ring of 5 to 8 atoms or a 5- to 8-membered cyclic imide;
$SR^5$, where R⁵ represents a $C_1$ to $C_6$ alkyl group; cycloalkyl; unsubstituted aryl; unsubstituted aralkyl; or unsubstituted heteroaryl, $C(O)R^6$, where R⁶ represents a $C_1$ to $C_6$ alkyl group; perfluorinated alkyl; cycloalkyl; unsubstituted aryl; unsubstituted aralkyl; unsubstituted heteroaryl; O—$C_1$ to $C_6$ alkyl; O-cycloalkyl; O-unsubstituted aryl; O-unsubstituted aralkyl; O-unsubstituted heteroaryl; or $N(R^7)(R^8)$;

with the proviso that when X represents $C(O)R^6$, then R⁶ represents a $C_1$ to $C_6$ alkyl group; perfluorinated alkyl; cycloalkyl; unsubstituted aryl; unsubstituted aralkyl; unsubstituted heteroaryl; or $N(R^7)(R^8)$;

R⁷ and R⁸, which may be identical or different, represent H; a $C_1$ to $C_6$ alkyl group; cycloalkyl cyclopropyl; unsubstituted aryl; unsubstituted aralkyl; or unsubstituted heteroaryl;

$OR^7$, where

R⁷ represents H; a $C_1$ to $C_6$ alkyl group; cycloalkyl; unsubstituted aryl; unsubstituted aralkyl; unsubstituted heteroaryl; C(O)—$C_1$ to $C_6$ alkyl; C(O)-cycloalkyl; C(O)-unsubstituted aryl; C(O)-unsubstituted aralkyl; C(O)-unsubstituted heteroaryl; C(O)O—$C_1$ to $C_6$ alkyl; C(O)O-cycloalkyl; C(O)O-unsubstituted aryl; C(O)O-unsubstituted aralkyl; C(O)O-unsubstituted heteroaryl; $(CH_2)_mCCR^8$; $(CH_2)_pCH=CR^8$;

where m=1 to 6 and p=1 to 6; or $CH_2OR^7$; $CH_2SR^5$; $CH_2NR^3R^4$; or $CH_2N_3$, provided that at least two of V, W, or Y represent H.

2. A compound of formula (I) according to claim 1, wherein R¹ represents methyl, $CF_3$, $CF_2CF_3$, $CH(CF_3)_2$, cyclopropyl, phenyl, or benzyl.

3. A compound of formula (I) according to claim 1, wherein R² represents a $C_1$ to $C_4$ alkyl group, phenyl, tolyl, or benzyl.

4. A compound of formula (I) according to claim 1, wherein R³ represents H, a $C_1$ to $C_4$ alkyl group, cyclopropyl, phenyl, or benzyl.

5. A compound of formula (I) according to claim 1, wherein R⁴ represents H, a $C_1$ to $C_4$ alkyl group, cyclopropyl, phenyl, benzyl, C(O)—$C_1$ to $C_4$ alkyl, C(O)-cyclopropyl, C(O)-phenyl, C(O)-benzyl, $C_1$ to $C_4$ alkyl, $SO_2$-cyclopropyl, $SO_2$-phenyl, $C(O)N(R^5)_2$ where R⁵ represents H or a $C_1$ to $C_4$ alkyl group, or cyclopropyl, or phenyl, or benzyl, $C(O)OR^6$ where R⁶ represents a $C_1$ to $C_4$, alkyl group, or benzyl.

6. A compound of formula (I) according to claim 1, wherein R⁵ represents a methyl, cyclopropyl, phenyl, or benzyl.

7. A compound of formula (I) according to claim 1, wherein R⁶ represents methyl, trifluoromethyl, cyclopropyl, phenyl, benzyl, unsubstituted heteroaryl, O-cyclopropyl, O-phenyl, O-benzyl, $N(R^7)(R^8)$ with the proviso that when X represents $C(O)R^6$, then R⁶ represents methyl, trifluoromethyl, cyclopropyl, phenyl, benzyl, or $N(R^7)(R^8)$, R⁷ and R⁸, which may be identical or different, represent H, methyl, cyclopropyl, phenyl, unsubstituted aralkyl, or benzyl.

8. A compound of formula (I) according to claim 1, wherein V, W, X, and Y independently represent $OR^7$, where R⁷ represents H, methyl, cyclopropyl, phenyl, benzyl, C(O)—$C_1$ to $C_4$ alkyl, C(O)-cyclopropyl, C(O)-phenyl, C(O)-benzyl, C(O)O—$C_1$ to $C_4$ alkyl, C(O)O-cyclopropyl, C(O)O-phenyl, C(O)O-benzyl.

9. A compound of formula (I) according to claim 1, wherein

U represents Cl,

V, W, and Y represent H, and

X represents:

Cl, Br, CN, or $N_3$;

$Si(R^a)(R^b)(R^c)$, where

Rᵃ, Rᵇ and Rᶜ, which may be identical or different, represent a $C_1$ to $C_6$ alkyl group or unsubstituted aryl group;

R¹, where

R¹ represents a $C_1$ to $C_6$ alkyl group; a $C_1$ to $C_6$ perfluoroalkyl group; cycloalkyl; unsubstituted aryl; unsubstituted aralkyl; or unsubstituted heteroaryl;

$S(O)_nR^2$, where n=0, 1, or 2,

R² represents a $C_1$ to $C_6$ alkyl group; unsubstituted aryl; unsubstituted aralkyl; or unsubstituted heteroaryl, $NR^3R^4$, where R³ represents H, a $C_1$ to $C_6$ alkyl group; cycloalkyl; unsubstituted aryl; unsubstituted aralkyl; or unsubstituted heteroaryl, R⁴ represents H; a $C_1$ to $C_6$ alkyl group; cycloalkyl; unsubstituted aryl; unsubstituted aralkyl; unsubstituted heteroaryl; C(O)—$C_1$ to $C_6$ alkyl C(O)-cycloalkyl; C(O)-unsubstituted aryl; unsubstituted C(O)-unsubstituted aralkyl; C(O)-unsubstituted heteroaryl; $SO_2$—$C_1$ to $C_6$ alkyl; $SO_2$-cycloalkyl; $SO_2$-unsubstituted aryl; $SO_2$-unsubstituted heteroaryl; $C(O)N(R^5)_2$; where R5 is as defined for R³; C(O)$OR^6$, where R⁶ represents a $C_1$ to $C_6$ alkyl group; or unsubstituted aralkyl; or R³ and R⁴ may be joined together to form a non-aromatic ring of 5 to 8 atoms or a 5- to 8-membered cyclic imide;

$SR^5$, where

R⁵ represents a $C_1$ to $C_6$ alkyl group; cycloalkyl; unsubstituted aryl; unsubstituted aralkyl; or unsubstituted heteroaryl, $C(O)R^6$, where R⁶ represents a $C_1$ to $C_6$ alkyl group; perfluorinated alkyl; cycloalkyl; unsubstituted aryl; unsubstituted aralkyl; unsubstituted heteroaryl; or $N(R^7)(R^8)$ R⁷ and R⁸, which may be identical or different, represent H; a $C_1$ to $C_6$ alkyl group; cycloalkyl; unsubstituted aryl; unsubstituted aralkyl; or unsubstituted heteroaryl;

$OR^7$, where

R⁷ represents H; a $C_1$ to $C_6$ alkyl group; cycloalkyl; unsubstituted aryl; unsubstituted aralkyl; unsubstituted heteroaryl; C(O)—$C_1$ to $C_6$ alkyl; C(O)-cycloalkyl; C(O)-unsubstituted aryl; C(O)-unsubstituted aralkyl; C(O)-unsubstituted heteroaryl; C(O)O—$C_1$ to $C_6$ alkyl; C(O)O-cycloalkyl; C(O)O-unsubstituted aryl; C(O)O-unsubstituted aralkyl; C(O)O-unsubstituted heteroaryl; $(CH_2)_mCCR^8$; $(CH_2)_pCH=CR^8$;

where m=1 to 6 and p=1 to 6;

$CH_2OR^7$; $CH_2SR^5$; $CH_2NR^3R^4$; or $CH_2N_3$.

10. A compound of formula (I) according to claim 1, where

U represents Cl,

V, W, and Y represent H, and

X represents:

Cl; Br; or CN;

R¹, where

R¹ is a $C_1$ to $C_6$ alkyl group; a $C_1$ to $C_6$ perfluoroalkyl group; or cycloalkyl;

$S(O)_nR^2$, where R² represents a $C_1$ to $C_6$ alkyl group;

$C(O)R^6$, where R⁶ represents a perfluorinated alkyl group; cycloalkyl;

$OR_7$, where $R^7$ represents a $C_1$ to $C_6$ alkyl group; a $C_1$ to $C_6$ perfluoroalkyl group; cycloalkyl;

$NR^3R^4$; where $R^3$ represents a $C_1$ to $C_6$ alkyl group; cycloalkyl, and $R^4$ represents a $C_1$ to $C_6$ alkyl group; cycloalkyl; or $R^3$ and $R^4$ are joined together to form a non-aromatic ring of 5 to 8 atoms or a 5- to 8-membered cyclic imide; or $CH_2OR^7$ where $R^7$ represents a $C_1$ to $C_6$ alkyl group; a $C_1$ to $C_6$ perfluoroalkyl group; cycloalkyl; $(CH_2)_mCCR^8$; $(CH_2)_pCH=CR^8$ where $R^8$ represents H, $Si(R^a)(R^b)(R^c)$, or $R^1$ and m=1 to 6 and p=1 to 6.

11. A compound of formula (I) according to claim 1, wherein
U represents Cl,
V, W, and Y represent H, and
X represents F, Cl, Br, $CF_3$, CN, $SO_2CH_3$, $CH_3$, $CH_2CH_3$, cyclopropyl, C(O)cPr, $C(O)CF_3$, $N(CH_3)_2$, $OCF_3$, or $CH_2OCH_2CCH$.

12. A drug comprising the compound of formula (I) according to claim 1.

13. A method for anti-inflammatory treatment comprising administering a therapeutically effective amount of a compound of formula (I) according to claim 1, to a subject in need thereof.

14. A method for treating vasculitis comprising administering a therapeutically effective amount of a compound of formula (I) according to claim 1 to a subject in need thereof.

15. A method for treating lupus erythematosus comprising administering a therapeutically effective amount of a compound of formula (I) according to claim 1 to a subject in need thereof.

16. A method for treating cancer comprising administering to a subject in need thereof a therapeutically effective amount of a compound of formula (I) according to claim 1 in association with an anti-cancer agent.

17. A method for anti-inflammatory treatment comprising administering to a subject in need thereof a therapeutically effective amount of a compound of formula (I'), its pharmaceutically acceptable salt, solvate or hydrate, in the form of an enantiomer or a mixture of enantiomers:

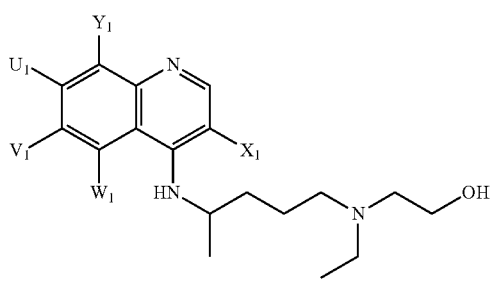

(I')

in which U1 represents:
F, Cl, Br, CN, $CF_3$, or $N_3$;
and $V_1$, $W_1$, $X_1$ and $Y_1$ independently represent I, $NO_2$ or H, provided that $V_1$, $W_1$, $X_1$ and $Y_1$ do not all simultaneously represent H.

18. A method for anti-inflammatory treatment comprising administering a therapeutically effective amount of a compound of formula (I') according to claim 17, wherein:
$U^1$ represents Cl,
$V_1$, $W_1$, and $Y_1$ represent H and $X^1$ represents I or $NO_2$.

19. A method for treating lupus erythematosus comprising administering to a subject in need thereof anti-inflammatory treatment a therapeutically effective amount of a compound of formula (I') as defined in claim 17, a pharmaceutically acceptable salt, solvate or hydrate thereof, in the form of an enantiomer or a mixture of enantiomers.

20. A method for treating lupus erythematosus comprising administering to a subject in need thereof a therapeutically effective amount of a compound of formula (I"), its pharmaceutically acceptable salt, solvate or hydrate in the form of an enantiomer or a mixture of enantiomers:

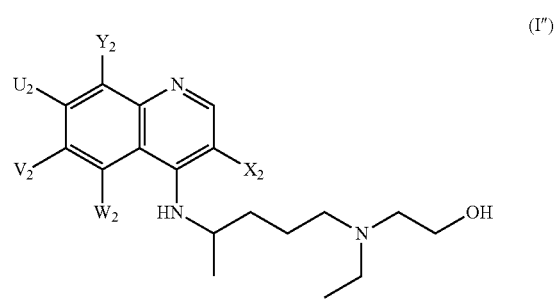

(I")

in which $U_2$ represents:
F, Cl, Br, CN, $CF_3$, or $N_3$;
and $V_2$, $W_2$, $X_2$ and $Y_2$ independently represent H, with the proviso that $V_2$, $W_2$, $X_2$ and $Y_2$ do not all simultaneously represent H, or $C(O)R^6$, where $R^6$ represents $O-C_1-C_6$ alkyl; O-cycloalkyl; O-aryl, O-aralkyl; or O-heteroaryl.

21. A method for treating lupus erythematosus comprising administering to a subject in need thereof a therapeutically effective amount of a compound of formula (I") according to claim 20, wherein:
$U_2$ represents Cl,
$V_2$, $W_2$, and $Y_2$ represent H and $X_2$ represents $C(O)R^6$, where $R^6$ represents $O-C_1-C_6$ alkyl; O-cycloalkyl; O-aryl, O-aralkyl; or O-heteroaryl.

22. A method for treating lupus erythematosus comprising administering to a subject in need thereof a therapeutically effective amount of a compound of formula (I') as defined in claim 17 association with an anticancer agent.

23. A method for treating vasculitis comprising administering to a subject in need thereof, a therapeutically effective amount of a compound of formula (I') as defined in claim 17.

24. The method of claim 16, wherein said cancer is colorectal cancer or lung cancer.

25. The method of claim 22, wherein said cancer is colorectal cancer or lung cancer.

26. A method for treating cancer in a subject in need thereof comprising administering a therapeutically effective amount of a compound of formula (I") as defined in claim 20, in association with an anticancer agent.

27. The method of claim 26, wherein said cancer is colorectal cancer or lung cancer.

28. A method for treating vasculitis comprising administering to a subject in need thereof a therapeutically effective amount of a compound of formula (I") as defined in claim 20.

* * * * *